United States Patent
Dudee

(10) Patent No.: US 11,890,055 B2
(45) Date of Patent: Feb. 6, 2024

(54) ACCOMMODATING INTRAOCULAR LENS ASSEMBLY

(71) Applicant: Jitander Dudee, Lexington, KY (US)

(72) Inventor: Jitander Dudee, Lexington, KY (US)

( * ) Notice: Subject to any disclaimer, the term of this patent is extended or adjusted under 35 U.S.C. 154(b) by 513 days.

(21) Appl. No.: 17/062,681

(22) Filed: Oct. 5, 2020

(65) Prior Publication Data

US 2021/0100651 A1     Apr. 8, 2021

Related U.S. Application Data

(60) Provisional application No. 62/910,018, filed on Oct. 3, 2019.

(51) Int. Cl.
| | | |
|---|---|---|
| *A61F 2/16* | (2006.01) | |
| *A61B 3/135* | (2006.01) | |
| *A61B 3/00* | (2006.01) | |
| *A61B 17/3205* | (2006.01) | |
| *A61F 9/007* | (2006.01) | |
| *A61F 2/48* | (2006.01) | |

(52) U.S. Cl.
CPC ............ *A61B 3/135* (2013.01); *A61B 3/0008* (2013.01); *A61B 3/0033* (2013.01); *A61B 3/0075* (2013.01); *A61B 17/32053* (2013.01); *A61F 2/164* (2015.04); *A61F 2/1618* (2013.01); *A61F 2/1632* (2013.01); *A61F 2/1651* (2015.04); *A61F 2/1656* (2013.01); *A61F 9/00754* (2013.01); *A61F 9/00763* (2013.01); *A61F 2/48* (2021.08); *A61F 2002/16901* (2015.04)

(58) Field of Classification Search
CPC ..... A61B 3/135; A61B 3/0008; A61B 3/0033; A61B 3/0075; A61B 17/32053; A61F 2/164; A61F 2/1651; A61F 2/1618; A61F 2/1632; A61F 2/1656; A61F 9/00754; A61F 9/00763; A61F 2002/16901; A61F 2/48

See application file for complete search history.

(56) References Cited

U.S. PATENT DOCUMENTS

| | | | |
|---|---|---|---|
| 3,305,294 A | | 2/1967 | Alvarez |
| 9,713,526 B2 | | 7/2017 | Rombach |
| 10,265,163 B2 | | 4/2019 | Dudee |
| 10,709,551 B2 | | 7/2020 | Dudee |
| 2010/0097569 A1* | 4/2010 | Weeber | .......... G02C 7/06 |
| | | | 623/6.3 |
| 2010/0318186 A1* | 12/2010 | Bumbalough | ........ A61F 2/1613 |
| | | | 623/6.43 |
| 2016/0184089 A1* | 6/2016 | Dudee | .......... A61F 2/1648 |
| | | | 623/6.22 |

(Continued)

*Primary Examiner* — Jerrah Edwards
*Assistant Examiner* — Aren Patel
(74) *Attorney, Agent, or Firm* — Black McCuskey

(57) ABSTRACT

An accommodating intraocular lens assembly can include a first lens, a first stanchion, a second lens, and a second stanchion. The first lens can have a first anterior side and a first posterior side. The first stanchion can have a first distal end connected to the first lens and a first base end. The second lens can have a second anterior side and a second posterior side. The second stanchion can have a second distal end connected to the second lens and a second base end. The first lens and the second lens can move laterally relative to one another during contraction of the ciliary muscle in a vertically-extending plane containing the optic axis of the eye and substantially centered in the eye.

11 Claims, 12 Drawing Sheets

(56) References Cited

U.S. PATENT DOCUMENTS

2017/0235113 A1* 8/2017 McCafferty ............. G02B 3/14
                                                    359/693
2019/0076242 A1* 3/2019 Pinto ...................... A61F 2/164
2021/0275294 A1* 9/2021 Zhang ................ A61B 1/00174

* cited by examiner

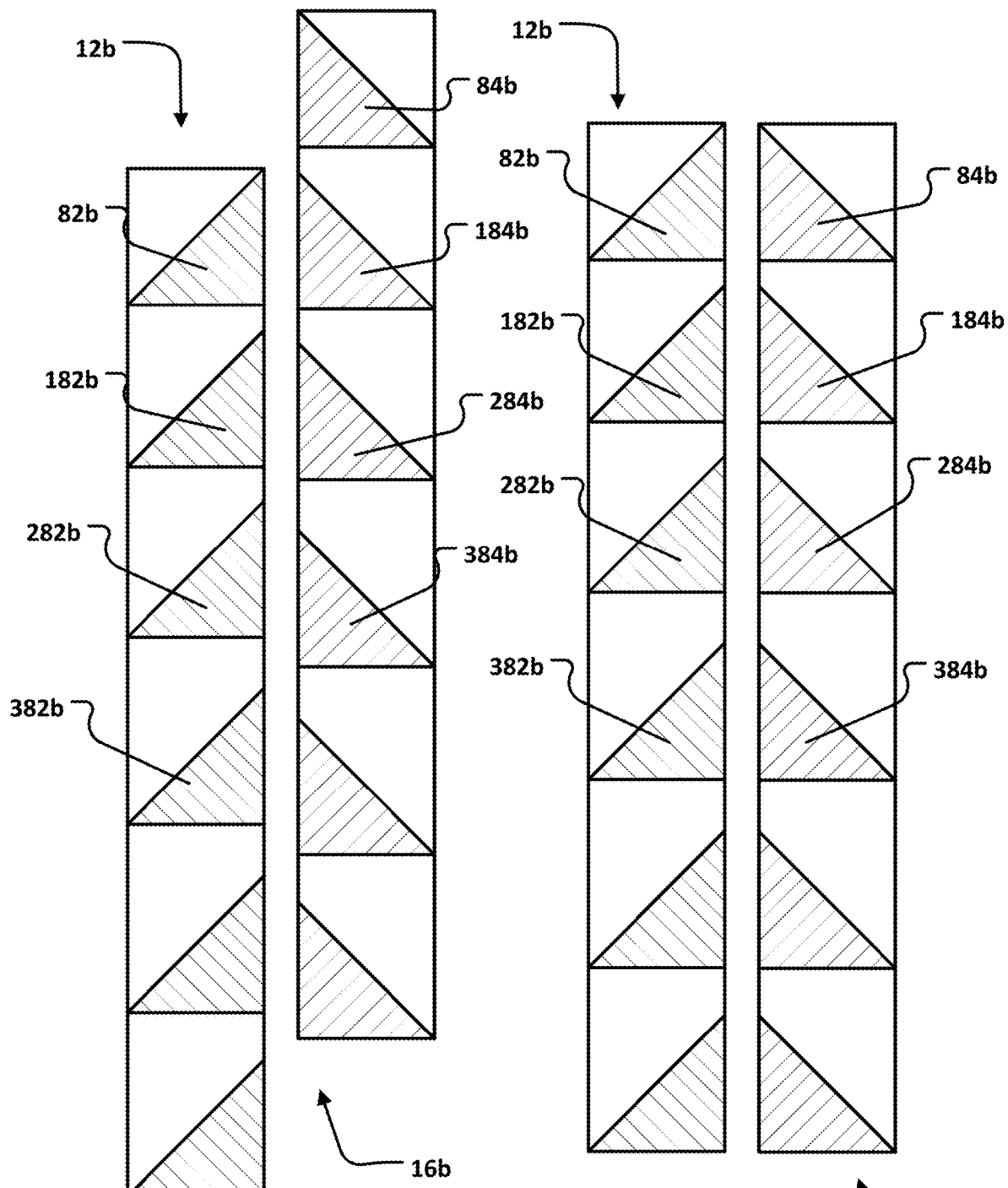

ACCOMMODATING INTRAOCULAR LENS ASSEMBLY

CROSS-REFERENCE TO RELATED APPLICATIONS

This application claims the benefit of U.S. Provisional Patent Application Ser. No. 62/910,018 for IMPROVEMENTS IN EYE CARE, filed on 2019 Oct. 3, which is hereby incorporated by reference in its entirety.

BACKGROUND

1. Field

The present disclosure relates to structures positionable in a human eye such as intraocular lens arrangements, drug delivery systems, sensor holders, and glaucoma treatment devices.

2. Description of Related Prior Art

Prosthetic intra-ocular lenses (IOLs) are routinely implanted following cataract extraction in human eyes and have grown in sophistication in order to provide better functional visual acuity with fewer troublesome distortions, reflections and aberrations to images focused on the retina. However, the natural lens retains distinct advantages over currently available IOLs. One such quality is the ability to alter its optical power to allow clear focusing on near as well as distant objects through human volition in tandem with contraction of the ciliary muscle of the eye. The physiological mechanism whereby the human eye voluntarily alters its focal point from distance to near is termed "near-accommodation" and a prosthetic lens implant that seeks to perform this function is termed an Accommodating IOL or AIOL. Several designs have been proposed in the prior art for AIOLS that attempt to achieve the variable focus distance of the youthful natural lens but all have significant limitations.

U.S. patent Ser. No. 10/265,163 discloses an accommodating intraocular lens assembly. A method of positioning an accommodating intraocular lens assembly in an eye can include implanting an accommodating intraocular lens assembly having a positive power lens in the eye. The accommodating intraocular lens assembly can also include a plurality of stanchions extending between base ends and distal ends. The base ends can be disposed in spaced relation to one another about a first arcuate periphery positioned in a ciliary sulcus of the eye. The distal ends can be disposed about a second arcuate periphery extending in a second plane positioned forward and outside of a capsular bag of the eye. The positive-power lens can be connected with the plurality of distal ends whereby a center of the positive power lens is moved along the central optic axis in response to contraction of the first arcuate periphery by contraction of the ciliary sulcus.

U.S. patent Ser. No. 10/709,551 also discloses an accommodating intraocular lens assembly. An accommodating intraocular lens assembly can include a first lens, a first plurality of stanchions, a second lens, and a second plurality of stanchions. A central optic axis can extend through centers of the first and second lenses. The first plurality of stanchions can each extend a first distance between a first base end and a first distal end. The first lens can be connected with the first distal ends. The second plurality of stanchions can each extend a second distance between a second base end and a second distal end. The second lens can be connected with the second distal ends. Compression at the peripheries of the stanchions induces movement of the lenses apart from one other.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

An accommodating intraocular lens assembly can include a first lens, a first stanchion, a second lens, and a second stanchion. The first lens can be configured for positioning in an eye and can have a first anterior side and a first posterior side. The first anterior side can face toward a pupil of the eye when the first lens is positioned in the eye and the first posterior side can face away from the pupil of the eye when the first lens is positioned in the eye. The first stanchion can have a first distal end connected to the first lens and can extend away from the first lens to a first base end. The first base end can be configured for positioning within a capsular bag of the eye or on a ciliary sulcus/muscle of the eye whereby contraction of the ciliary sulcus/muscle during accommodation of the eye moves the first base end towards an optic axis of the eye. The second lens can be configured for positioning in the eye with the first lens and can have a second anterior side and a second posterior side. The second anterior side can face the first posterior side when the first lens and the second lens are positioned in the eye and the second posterior side can face into to the eye when the second lens is positioned in the eye. The second stanchion can have a second distal end connected to the second lens and can extend away from the second lens to a second base end. The second base end can be configured for positioning within the capsular bag of the eye or on the ciliary sulcus/muscle of the eye whereby contraction of the ciliary sulcus/muscle during accommodation of the eye moves the second base end towards the optic axis of the eye. The first lens and the second lens can move laterally relative to one another during contraction of the ciliary sulcus/muscle in a vertically-extending plane containing the optic axis of the eye and substantially centered in the eye.

An accommodating intraocular lens assembly can include a first lens, a first stanchion, a second lens, and a second stanchion. The first lens can be configured for positioning in an eye and can have a first anterior side and a first posterior side. The first anterior side can face toward a pupil of the eye when the first lens is positioned in the eye and the first posterior side can face away from the pupil of the eye when the first lens is positioned in the eye. The first stanchion can have a first distal end connected to the first lens and can extend away from the first lens to a first base end. The first base end can be configured for positioning within a capsular bag of the eye or on a ciliary sulcus/muscle of the eye whereby contraction of the ciliary sulcus/muscle during accommodation of the eye moves the first base end towards an optic axis of the eye. An axis extending between the first base end and the first distal end does not intersect the optic axis of the eye. The second lens can be configured for positioning in the eye with the first lens and can have a second anterior side and a second posterior side. The second anterior side can face the first posterior side when the first lens and the second lens are positioned in the eye and the second posterior side can face into to the eye when the second lens is positioned in the eye. The second stanchion can have a second distal end connected to the second lens and can extend away from the second lens to a second base end. The second base end can be configured for positioning within the capsular bag of the eye or on the ciliary sulcus/muscle of the eye whereby contraction of the ciliary sulcus/muscle during accommodation of the eye moves the second base end towards the optic axis of the eye. An axis extending between the second base end and the second distal end does not intersect the optic axis of the eye. The first stanchion and the second stanchion are configured such that the first lens and the second lens rotate relative to one another about the optic axis of the eye during contraction of the ciliary sulcus/muscle.

An accommodating intraocular lens assembly can include a first lens, a first stanchion, a second lens, and a second stanchion. The first lens can be configured for positioning in an eye and can have a first anterior side and a first posterior side. The first anterior side can face toward a pupil of the eye when the first lens is positioned in the eye and the first posterior side can face away from the pupil of the eye when the first lens is positioned in the eye. The first stanchion can have a first distal end connected to the first lens and can extend away from the first lens to a first base end. The first base end can be configured for positioning within a capsular bag of the eye or on a ciliary sulcus/muscle of the eye whereby contraction of the ciliary sulcus/muscle during accommodation of the eye moves the first lens along an optic axis of the eye. The second lens can be configured for positioning in the eye with the first lens and can have a second anterior side and a second posterior side. The second anterior side can face the first posterior side when the first lens and the second lens are positioned in the eye and the second posterior side can face into to the eye when the second lens is positioned in the eye. The second stanchion can have a second distal end connected to the second lens and can extend away from the second lens to a second base end. The second base end can be configured for positioning within the capsular bag of the eye or on the ciliary sulcus/muscle of the eye whereby contraction of the ciliary sulcus/muscle during accommodation of the eye moves the second lens along the optic axis of the eye. A shape of the first lens is an aperture-less disc and a shape of the second lens is a disc with a centered aperture.

An accommodating intraocular lens assembly can include a first lens, a first stanchion, a second lens, and a second stanchion. The first lens can be configured for positioning in an eye and can have a first anterior side and a first posterior side. The first anterior side can face toward a pupil of the eye when the first lens is positioned in the eye and the first posterior side can face away from the pupil of the eye when the first lens is positioned in the eye. The first stanchion can have a first distal end connected to the first lens and can extend away from the first lens to a first base end. The first base end can be configured for positioning within a capsular bag of the eye or on a ciliary sulcus/muscle of the eye whereby contraction of the ciliary sulcus/muscle during accommodation of the eye moves the first lens along an optic axis of the eye. The second lens can be configured for positioning in the eye with the first lens and can have a second anterior side and a second posterior side. The second anterior side can face the first posterior side when the first lens and the second lens are positioned in the eye and the second posterior side can face into to the eye when the second lens is positioned in the eye. The second stanchion can have a second distal end connected to the second lens and can extend away from the second lens to a second base end. The second base end can be configured for positioning within the capsular bag of the eye or on the ciliary sulcus/muscle of the eye whereby contraction of the ciliary sulcus/muscle during accommodation of the eye moves the second lens along the optic axis of the eye. The first posterior side defines a first surface and the second anterior side defines a second surface and wherein the first surface and the second surface are mirrored in shape with respect to one another and interlock when the first lens and the second lens move due to contraction of the ciliary sulcus/muscle during accommodation.

An accommodating intraocular lens assembly can include a first lens, a first stanchion, a second stanchion, a second lens, a third stanchion, a fourth stanchion, a fifth stanchion, a sixth stanchion, a third lens, a seventh stanchion, and an eighth stanchion. The first lens can be configured for positioning in an eye and can have a first anterior side and a first posterior side. The first anterior side can face toward a pupil of the eye when the first lens is positioned in the eye and the first posterior side can face away from the pupil of the eye when the first lens is positioned in the eye. The first stanchion can have a first distal end connected to the first lens and can extend away from the first lens to a first base end. The second stanchion can have a second distal end connected to the first lens and can extend away from the first lens to a second base end. The second lens can be configured for positioning in the eye with the first lens and can have a second anterior side and a second posterior side. The second anterior side can face the first posterior side when the first lens and the second lens are positioned in the eye and the second posterior side can face away from the pupil of the eye when the second lens is positioned in the eye. The third stanchion can have a third distal end connected to the second lens and can extend away from the second lens to the first base end. The first stanchion and the third stanchion can be merged at the first base end. The fourth stanchion can have a fourth distal end connected to the second lens and can extend away from the second lens to the second base end. The second stanchion and the fourth stanchion can be merged at the second base end. The first base end and the second base end can be configured for positioning within the capsular bag of the eye or on the ciliary sulcus/muscle of the eye whereby contraction of the ciliary sulcus/muscle during accommodation of the eye moves the first lens along the optic axis of the eye. The fifth stanchion can have a fifth distal end connected to the second lens and can extend away from the second lens to a third base end. The sixth stanchion can have a sixth distal end connected to the second lens and can extend away from the second lens to a fourth base end. The third lens can be configured for positioning in the eye with the first lens and the second lens. The third lens can have a third anterior side and a third posterior side. The third anterior side can face the second posterior side when the second lens and the third lens are positioned in the eye and the third posterior side can face away from the pupil of the eye when the third lens is positioned in the eye. The seventh stanchion can have a seventh distal end connected to the third lens and can extend away from the third lens to the third base end. The fifth stanchion and the seventh stanchion can be merged at the third base end. The eighth stanchion can have an eighth distal end connected to the third lens and can extend away from the third lens to the fourth base end. The sixth stanchion and the eighth stanchion can be merged at the fourth base end. The third base end and the fourth base end can be configured for positioning within the capsular bag of the eye or on the ciliary sulcus/muscle of the eye whereby contraction of the ciliary sulcus/muscle during accommodation of the eye moves the third lens along the optic axis of the eye.

An accommodating intraocular lens assembly can include a lens, at least one stanchion, and a shell. The lens can be centered on an optic axis and can be configured for positioning in an eye. The lens can have a first anterior side and a first posterior side. The first anterior side can face toward a pupil of the eye when the lens is positioned in the eye and the first posterior side can face away from the pupil of the eye when the lens is positioned in the eye. The at least one stanchion can have a distal end connected to the lens and can extend away from the lens to a base end. The at least one stanchion can be substantially straight in a plane containing the optic axis. The shell can have the shape of less than a full ring torus, wherein the shell can extend three hundred and sixty degrees about the optic axis in the toroidal direction and can extend no greater than one hundred and eighty degrees about a poloidal center of curvature. The shell can have an outer perimeter radially furthest from the optic axis and an inner perimeter radially closest to the optic axis. The base end of the at least one stanchion can be connected to the inner perimeter. The lens, the at least one stanchion, and the shell can be configured to be positioned in contact with an iris of the eye whereby contraction of the ciliary sulcus/muscle during accommodation of the eye moves the iris against the shell and causes the shell to invert such that the poloidal center of curvature moves from a first side of the shell along the optic axis to a second side of the shell that is opposite to the first side of the shell, further whereby the lens moves in a direction collinear to the optic axis.

BRIEF DESCRIPTION OF THE DRAWINGS

The detailed description set forth below references the following drawings:

FIG. 8 is a first vertical cross-section through a portion of an accommodating intraocular lens assembly according to another exemplary embodiment of the present disclosure;

FIG. 9 is a second vertical cross-section through the portion of the accommodating intraocular lens assembly shown in FIG. 8;

DETAILED DESCRIPTION

Figure 1:
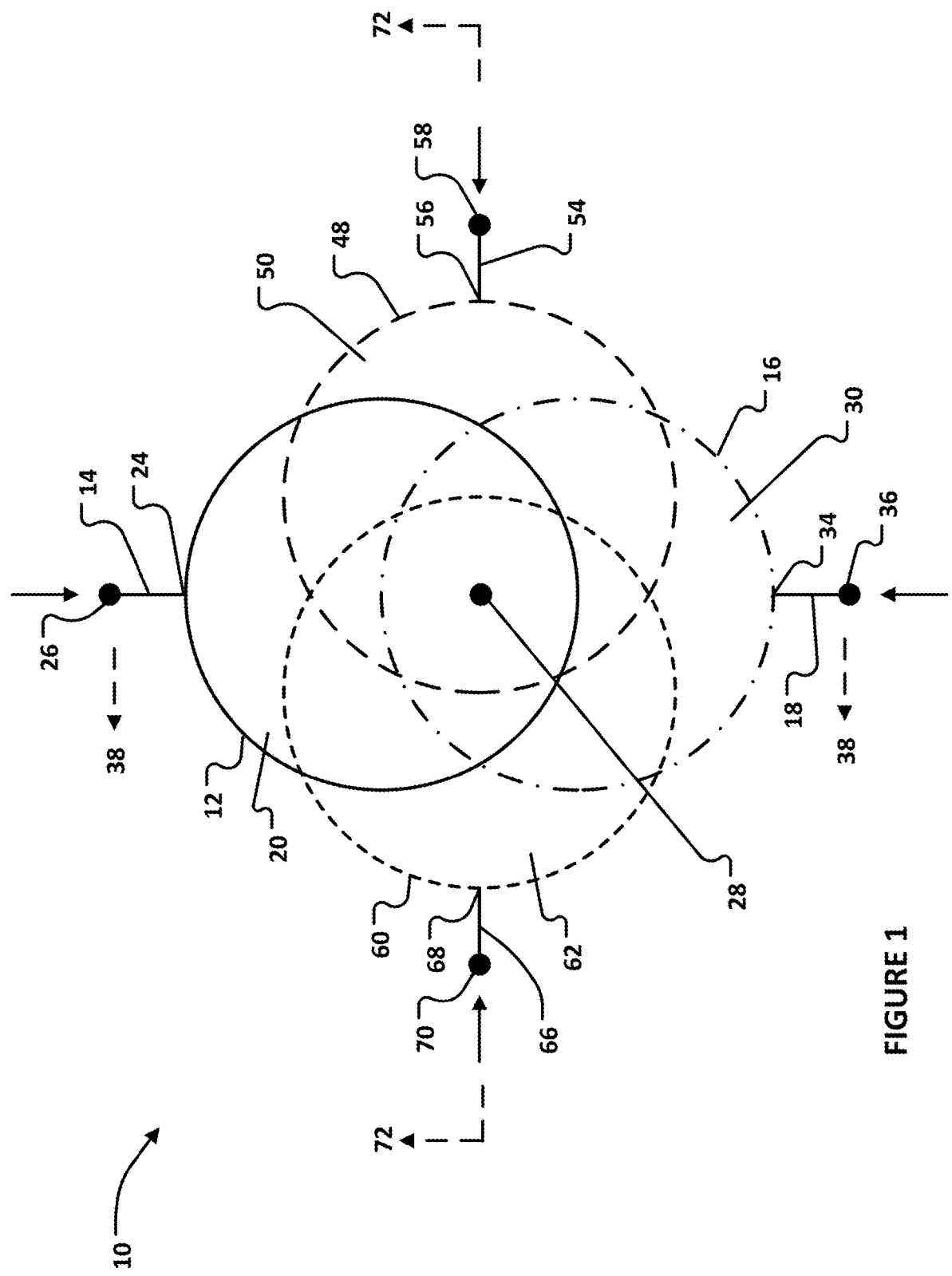
FIG. 1 is a schematic front view of an accommodating intraocular lens assembly according to an exemplary embodiment of the present disclosure.

A plurality of different embodiments of the present disclosure is shown in the Figures of the application. Similar features are shown in the various embodiments of the present disclosure. Similar features across different embodiments have been numbered with a common reference numeral and have been differentiated by an alphabetic suffix. Similar features in a particular embodiment have been numbered with a common two-digit, base reference numeral and have been differentiated by a different leading numeral. Also, to enhance consistency, the structures in any particular drawing share the same alphabetic suffix even if a particular feature is shown in less than all embodiments. Similar features are structured similarly, operate similarly, and/or have the same function unless otherwise indicated by the drawings or this specification. Furthermore, particular features of one embodiment can replace corresponding features in another embodiment or can supplement other embodiments unless otherwise indicated by the drawings or this specification.

The following terms are useful in the defining the operating environment of one or more embodiments of the present disclosure:

Intra-ocular Lens or "IOL" refers to a prosthetic optical lens placed within the eye to allow better visual functioning of the eye;

"Conventional IOL" refers to an IOL that has a single fixed focal point (also known as a monofocal IOL);

"Near Accommodation" or "Accommodation" refers to a change in the focal point of the optical system of the human eye from fixation on distant objects (those further away than about 6 meters from the eye) to near objects (those closer than about 0.5 meters from the eye), the term "accommodation" also includes the act of focusing on objects in the intermediate range of 6 to 0.5;

"Ciliary Body" or "CB" refers to the Ciliary Body of the eye including the various neuromuscular elements comprising the structure commonly referred to as the Ciliary Muscle, as well as the connective tissue joining the muscular elements and forming attachments of the ciliary muscle to the sclera and to the zonules or suspensory ligaments of the lens capsule. The muscular tissue within the CB is generally of the type known as "smooth muscle". Many microscopic muscle cells are connected to each other via elastic connective tissue forming bundles or rings of muscle that contract and stretch as a result of the combined contraction of the constituent muscle fibers;

"Ciliary Body accommodation" or "CBA" refers to the anatomical and physiological changes initiated by the act of voluntary human accommodation, during CB accommodation, impulses from the brain are transmitted to the nerves supplying the ocular tissues so that at least one eye is directed to align its optic axis towards the object of visual fixation, when at least one eye fixates on an object of visual interest, subconscious cues create an approximate estimate of the distance of the object from the eye and CB accommodation is triggered to the appropriate approximate extent required for the image from the object to be sharply focused on the retina, a process of reiterative biofeedback occurs so that the degree of CB accommodation is matched to the required working distance for sharp focus of the image from the object that is being viewed, other physiological actions are also linked to CB accommodation such as convergence (inwards rotation of eyes to triangulate and focus on a near object) and miosis (constriction of pupils to increase visual depth of field);

"Lenticular accommodation" refers to the alteration in optical power of the youthful or pre-presbyopic human eye in response to CB accommodation, the natural human lens is also known as the crystalline lens. It is enclosed within the lens capsule which in turn is connected to the ciliary body via many zonules (also known as suspensory ligaments) that attach close to the peripheral equator of the lens capsule on its posterior and anterior surfaces and extend in a radial fashion, suspending the crystalline lens from the CB. CB accommodation results in increased relative curvature of the front and rear lens capsule surfaces (also known collectively as the capsular bag), and a forward shift in the optical center of the crystalline lens, lenticular accommodation occurs as a result of decreased radial tension in the zonules because CB accommodation causes a relative anterior shift of the ring formed by the center of radial suspension the zonules, the cross sectional diameter of the eyeball is less at the relatively anterior location of the CB ring during CB accommodation, therefore the tension in the zonules is decreased allowing the elastic crystalline lens to revert to a shape that is more rounded in its anterior and posterior curvatures;

"Ciliary Sulcus" Refers to the ring like space bounded posteriorly by the ciliary process and suspensory ligaments of the lens (zonules) and bounded anteriorly by the posterior surface of the iris, the ciliary sulcus is bounded peripherally by the soft tissues overlying the ciliary body, these soft tissues separate the ciliary sulcus from the muscular components of the ciliary body, specifically the circular or annular portions of the ciliary muscle, the meridional portions of the ciliary muscle lie more peripherally and are anchored at the scleral spur, the ciliary sulcus extends for 360 degrees at the base of the iris, is vertically oval in humans and decreases in diameter during CBA;

"UBM" or "Ultrasound biomicroscopy" refers to imaging studies of the eye which show characteristic biometric changes that occur during ciliary body contraction, for understanding of the intended working of embodiments of this present disclosure, it is necessary to define some biometric features that change during CBA:

SSD (sulcus-to-sulcus diameter)—distance between opposite points in the ciliary sulcus, this will vary between individuals due to normal anatomic differences depending on the axial location of the opposite points because the ciliary sulcus is oval instead of circular in the near accommodated state in comparison to the relaxed state as CBA reduces SSD, ICPA (Iris-ciliary process angle)—the angle between the plane of the iris and the direction of the ciliary process from between which the lens zonules extend to the equator of the capsular bag, ACA (anterior chamber angle)—the angle between the plane of the peripheral iris and the inner layer of the cornea where they meet close to the iris root;

"Annular muscle contraction" or "AMC" refers to the morphological changes occurring during the contraction and relaxation of an annular or sphincteric muscle, specifically, it relates to the shape changes of the round portion of the ciliary muscle during CBA, the ring shaped "round" portion of the ciliary muscle encloses a central opening known as a lumen, which forms the external boundary of the ciliary sulcus, when an annular muscle contracts its total volume remains essentially unchanged but the circle surrounding the lumen in the plane of the lumen constricts, each point lining the lumen moves in relation to its neighbor during contraction and relaxation so that there are no two points that remain stationary relative to each other;

"Elastic biological surface" or "EBS" refers to a flexible membrane that forms the outside enclosure of an annular muscle or other elastic biological surface such as the capsule (or capsular bag) of the crystalline lens;

"Point-to-point contraction linking" or "PPCL" refers to the ability of a device to remain in contact with an elastic biological surface during the entire cycle of contraction and expansion without slipping at its contact points and without offering sufficient resistance to impede movement or cause damage by abrasion or penetration, for a device to be usefully coupled to an annular muscle (such as that found in the CB) it is essential for the device to offer in a predictable manner only as much resistance to movement as is necessary to convert the contraction of the muscle (in this case the contraction associated with CBA) into useful work (in this case IOL accommodation or "IOLA"), effective PPCL depends on critical design elements related to the points of contact of the device to the elastic biological surface, the features in point of contact design to achieve effective PPCL include:

distribution and location—Points of contact should be located around a center of movement that is also the center of movement of the elastic biological surface, number—The points of contact should be numerous enough to maintain stable attachment during motion and distribute resistance evenly across biological surface, at least eight contact points can be desirable for PPCL to a device within the lumen of an annular muscle, too many points of contact if large will limit movement by causing crowding and if small, may impede biological function by causing scarring, size—large contact points in contact with elastic biological surfaces such as the ciliary sulcus or capsular bag will present resistance against contraction or expansion of those surfaces, the continuous expansion and contraction of an annular muscle (even with its surrounding connective tissue) against an inelastic surface is likely to cause damage to biological tissues by abrasion and deposition of eroded tissues, contact points that are too small are likely to cause damage by perforation or penetration into biological tissue, profile—curved contact points offer a variable surface area and some degree of "rocking" during expansion and contraction which protects biological tissue and reduces scarring, multiple protrusions are vulnerable to becoming entangled during implantation, becoming damaged or causing damage to biological tissue;

"Haptic Vaulting" when used in relation to IOLs refers to forward or backward movement of IOL optic in the direction of the visual axis relative to the distal ends of its haptics, in prior art Haptic vaulting is envisioned as a mechanism for achieving IOLA in capsular bag fixated IOLs in response to decreasing diameter of the capsular bag which may vertically compress the haptic ends, Haptic Vaulting may occur surreptitiously in even prior art conventional or monofocal IOLs, depending on nature and placement of the haptics within a fibrosed or contracted capsular bag;

"Rigid Vaulting" when used in relation to IOLs refers to forward or backward movement of IOL optic in the direction of the visual axis relative to the optical nodal point of the eye in response to mechanical forces within the eye, specifically, this relates to movement of an IOL fixed within a capsular bag (IOL-capsule diaphragm) in response to movements of the entire capsular bag caused by:

contraction or relaxation of the zonules attached to the capsular bag secondary to ciliary muscle contraction, variations in fluid pressure (from aqueous humor or vitreous humor) between the anterior and posterior surfaces of the IOL-capsule diaphragm, gravitational shifting of IOL in response to changes in eye position (Rigid Vaulting is widely believed to occur surreptitiously in prior art conventional or monofocal IOLs, but to a variable and unpredictable extent and therefore cannot be relied on to provide useful degree of IOLA);

"Pseudo-accommodation" refers to the retention of some functional unaided near vision in combination with good distance vision following cataract extraction in patients who do not have IOLA, in patients who have a fixed focal length IOL implanted, whose power is set for clear distant vision, it is the ability of such patients to have better than expected (although still limited) near vision (without reading glasses), its existence is due to the following factors or fortuitous conditions:

Pinhole effect—increased depth of field caused by decreasing aperture of the pupil during CBA and in conditions of high illumination, this effect may be enhanced in some lenses whose central curvature is higher than peripheral so that when the peripheral cornea is curtained off by the constricting pupil, the overall focus of the lens because closer, relying on the pinhole effect has the disadvantage of reducing amount of light available to the eye and hence compromising the overall quality of vision, Aspheric optic property of the IOL (Lens has more than one major focal point). This may be intentional or serendipitous: Multifocal IOL design including pupil independent (diffractive lenses, aspheric curvatures) and pupil assisted (linked to pupillary constriction like the pinhole effect but accentuated by the IOL deliberately having a higher power in its central curvature, and Fortuitous/serendipitous optical effects presenting a secondary near image due to lens tilt (induced lenticular astigmatism) and corneal myopic astigmatism (Asymmetry of corneal curvature or tilting of the IOL can cause astigmatism, for example in which vertical lines far away, are seen better than horizontal lines, with the reverse holding try for near, since writing tends be composed of vertical and horizontal lines, people with just the right degree of astigmatism learn to decode the otherwise blurred near vision), and Limited accommodation due to IOL forward movement during CBA which may occur with any IOL implanted in elastic capsular bag with intact zonular attachments where the IOL-capsular bag complex moves forward during CBA increasing the effective power of the IOL and causing its focal point to move from distance to near, younger post cataract patients are often seen to have less need for reading glasses than expected when their (non-accommodating) IOLs have been selected for distant focus in both eyes, it is thought that the combination of a vigorous scarring response (causing the posterior capsule to bind firmly around the edge of the lens, and still strong ciliary muscles, allows the IOL to move forward in a way similar to the natural lens, this effect is usually not of sufficient extent to obviate the need for reading glasses;

"Monovision" refers to the illusion of good near and far vision obtained by implanting a monofocal IOL in one eye whose focal point is for distance and another monofocal IOL in the fellow eye whose focal point is for near. Monovision can also achieve a form of pseudo-accommodation so that when both eyes are used together, one provides good monocular distance vision and the other provides acceptable monocular near vision if the brain is able to adapt to this method of correction, this technique is often not well tolerated and causes reduction in stereoscopic vision, the patient is able to use each eye for its working distance (distance or near) although this does not represent true accommodation;

"IOL accommodation" or "IOLA" refers to a change in the optical focal point of an intraocular lens (hereafter IOL) from a sharp distant focus to a sharp near focus (and intermediate distances when the object of visual attention is in between) in an attempt to simulate is lenticular accommodation in response to CB accommodation, IOL accommodation is not equivalent to the IOL multifocality achieved by multifocal IOLs described immediately below;

"Multifocal IOL" or "MFIOL" refers to an IOL designed to have multiple simultaneous focal point, MFIOLs offer a degree of pseudo accommodation by having multiple focal powers or curvatures molded into a single IOL resulting in images of objects at more than one working distance becoming focused simultaneously on the retina, however, the simultaneous presentation of more than one image by the IOL causes degradation and compromise of each of the images as well as troublesome visual symptoms of halos, glare, ghost images collectively known as dysphotopsia, the providential persistence of pupillary miosis associated with CB accommodation can be utilized to preferentially select the central portion of the IOL curvature for near focusing and allow input from the peripheral lens curvature when CB accommodation is relaxed, and the pupil becomes relatively dilated, however, this type of "pinhole effect" also compromises overall quality of the images and multifocal IOLs in general have limited utility because CB accommodation does not result in true IOL accommodation, the increased range of focus depth of field presented by a static multifocal IOL is offset by lower image quality and visual aberrations, the eye and brain have to learn to ignore the images that are not useful for the current working distance and therefore there is compromise in overall vision quality and comfort;

"Haptic" refers to an arrangement of structural elements whose primary purpose is to hold, support, maintain and fixate one or more other distinct elements or device within the eye, where the device serves a biologically important function;

"Haptic Passenger" refers to a functionally important device supported by the haptic, examples of Haptic Passengers and their associated functions include an optical lens system, a reservoir, depot or container for a therapeutic substance or drug, a diagnostic instrument or sensor;

"IOL haptic" or refers to a structural element of an IOL designed to hold an IOL in place within the eye, such as a haptic whose haptic passenger is a lens;

"IOL optic" refers to the optically active component of the IOL having light transmitting refractive power, such as the haptic passenger for an IOL haptic;

"Capsular bag" or "bag" refers to the partially elastic biological membrane which normally contains the lentil shaped crystalline lens of the eye between a front surface (anterior capsule) and a back surface (posterior capsule) which join at the equator of the capsular bag from which equator the lens is suspended from and connected to the processes of the ciliary body by zonules (or suspensory ligaments of the lens), the capsular bag is opened during cataract surgery to remove the cataractous lens by making a roughly circular opening in its anterior capsule, the capsular bag has traditionally been the desired location in which to place an IOL after cataract extraction, the IOL is normally placed through the anterior capsular opening or "rhexis" so that its spring like supporting haptics rest in or close to the equator of the bag, suspending the optic of the IOL within and perpendicular to the visual axis;

"Capsulorhexis" or "rhexis" refers to the surgical opening made in the capsular bag and is a vital step in modern cataract surgery, it is necessary to access the cataract for removal and to insert an IOL if it is to be placed in the capsular bag, and the terms "rhexis" and "incision" are used interchangeably herein;

"Posterior capsular fibrosis" or "Posterior capsular opacification" (PCO) refers to the migration and proliferation of fibroblast inside and around the remnants of the capsular bag following cataract surgery, in addition to reducing vision, the scar tissue formed by these fibroblasts causes scarring and contracture of the capsular bag resulting in loss of its elastic properties, posterior capsular fibrosis occurs to at least some extent in the majority of patients following cataract despite various precautions commonly taken to reduce it, contracture of the capsular bag can cause tilt or displacement of an IOL in contact with the bag and will limit post-operative capsular bag movement in response to CBA, the severity of posterior capsular fibrosis is unpredictable but often warrants YAG laser capsulotomy after surgery to break open the capsule when it interferes with vision, the behavior of the capsular remnants following YAG laser capsulotomy is even more unpredictable, this means that any AIOL that relies on capsular bag contraction for functioning is unlikely to be successful because CBA cannot be reliably translated into IOLA by the post-surgical capsular bag;

"Accommodating IOL" or "AIOL" refers to a prosthetic lens or IOL that seeks to restore the function of lenticular accommodation (other than by pseudo-accommodation or monovision) in a patient whose crystalline lens has been removed;

"Simple lens" refers to the concave and convex cross sections depicted in optical drawings and ray diagrams shown commonly in physics textbooks, wherein the convex or concave surfaces enclose a medium whose refractive index is different to that of the media in front and behind the lens, although its front and rear surfaces are separated such a lens has a point (which can actually lie outside the body of the lens) known as the optical center of the lens whose location and optical properties can be described in an idealized fashion by "Thin Lens Theory", and in a more complex, and potentially more accurate fashion by "Thick Lens Theory", the power of such a lens is normally fixed and does not change because the lens is solid and static, the power of a particular simple lens can be made different to that of another by altering one or both of the front and rear curvatures or the refractive index of the medium behind and/or in front of the lens;

"Compound lens" refers to a lens composed of two or more simple lenses whose overall optical parameters can be varied by varying the power of each component lens, varying the separation between the optical centers of the component lenses, and varying other spatial relationship (such as tilt and alignment) between the optical centers or surfaces of the component lenses;

"Flexible lens" refers to a lens composed of an optical medium which is fluid or gel like in mechanical property, and of essentially constant volume, and whose volume is contained and bounded across at least part of its surface by an elastic or flexible membrane, the power of a flexible lens can be varied by shape change of the fluid or gel like medium when such shape changes result in variations in curvature of the flexible membrane when the membrane lies across the visual axis, variation in separation of the front and back surfaces, and variation in location of optical center of lens;

"Biological lens" refers to a lens with front and back surfaces whose body is composed of regions of varying refractive index without clear demarcation or interface between the zones, the regions may be distributed so that the gradient in refractive index varies perpendicular to its optic axis (refractive index changing from center to periphery in a concentric radial fashion) and/or varies in the line of the optic axis so that the refractive index is maximum at the front surface, back surface or center of the lens, variations of the power of a biological lens can be achieved by a spatial redistribution of the regions of high and low refractive indices and may be achieved by overall change in the shape of the lens when it is contained within a flexible membrane or redistribution of the optical centers of the regions of different refractive index without overall shape change of the external boundaries of the lens capsule, resulting in a shifting of the optical center of the lens;

"Neo-biological lens" refers to a lens composed of material whose refractive index can be varied be electronic or photo-chemical means either across the entire material of the lens, or selectively in certain regions; and "Higher Order Aberrations" or "HOA" relates to imperfections of focusing of a nature more complex than lower order optical aberrations such as spherical error and astigmatism, clinically important examples of HOA include spherical aberration, coma and trefoil, correction of HOA can improve visual quality and satisfaction following ocular surgery.

The exact nature and relative importance of various physiological mechanisms active in the human eye during the act of accommodation is controversial. The theory of Helmholtz appears to be the most favored. It is agreed that contractions of the ciliary body/muscle occur in response to neural signals from the brain when accommodation is voluntarily or reflexly initiated. It is also agreed that in the youthful eye, this contraction causes several mechanical changes that result in the optical diopteric power of the lens system becoming more positive and so shifting the focal point of the lens closer to the person. The optical power change is thought to result from an anterior shift of the overall optical center of the lens closer to the cornea and an increase in curvature of the anterior and/or posterior refracting surfaces of the lens (necessitated by the requirement to maintain constant volume within the enclosing capsular bag) when the lentil shaped lens decreases in circumference at its attachment points (zonular fibers) in the plane roughly perpendicular to the visual axis.

In practice, other subtle changes may also contribute to a lesser extent such as constriction of the pupil to induce a pin-hole effect to increase depth of field—pseudo accommodation, shift of the constricted pupillary center away from the relaxed pupillary center to preferentially select a new optical line of site within the eye of different refractive power, and change in lens shape may cause shifting of relative position within the lens, of areas of differing pliability, elasticity and refractive index to cause a change in overall power.

For AIOL design a clear understanding of the anatomical changes occurring in the eye during CBA is desirable. In some species, CBA results in muscular activity that alters the curvature of the cornea or the length of the eyeball amongst other changes, but in humans, alterations of the shape and location of the crystalline lens appear to be the main mediators of accommodation.

When CBA is initiated in humans, at least three muscular sub systems within the ciliary body are activated. First, there is an annular or circular component—a sphincter muscle in the shape of a toroid in a plane approximately perpendicular to the visual axis, located internally to the scleral coat of the eye within the partially elastic parenchyma or connective tissue of the CB. This annular component contracts on accommodation so that the toroid becomes smaller in diameter and thicker in its cross section while the plane of the toroid moves closer to the front of the eye in the line of the visual axis. This contraction releases tension on the lens zonules and capsular bag, thereby causing forward movement of the optical center of the lens and a reduction in the equatorial diameter of the lens capsule.

Second, meridional or longitudinal components that run in approximately parallel to each other slight curve under the sclera connection their relatively stationary attachment on the sclera at one end to the pars plana of the ciliary body at the other end. The effect of contraction of these fibers is to pull the area of attachment of lens zonules anteriorly along the interior surface of the eyeball as it approaches the cornea. The anatomy of the anterior eyeball is such so that this movement results in release in tension of the lens zonules, especially those connecting to the front surface of the lens capsule so that the lens returns to a more rounded shape and its optical center moves forward. The annular fibers of the ciliary muscle lie in a ring separated from the sclera and eyeball by the longitudinal fibers so that the contraction of the longitudinal fibers mechanically facilitates the contraction of the annular components by occupying and increasing the space between the outer aspect of the ring muscles and the sclera.

Third, oblique fibers that run a semi-spiral course under the sclera of the eyeball. They likely act as slings to reduce forces that might inwardly detach the pars plana of the ciliary body and prevent wrinkling of the pars plana of the ciliary body during CBA.

Although the ciliary muscle is usually depicted in cross section, it is actually a complex 3-D structure that is fixed at its outside margin to the sclera of the eyeball and whose inside margin suspends the zonules which connect to the capsular bag. Different species have at least three types of muscle fibers within the ciliary muscle. The exact contribution of the various mechanisms linked to accommodation are not fully known but for the purpose of at least some embodiments of the present disclosure the important points are that when contracted during accommodation the ciliary muscle concentrates into a toroid which decreases in inside diameter, increases in cross sectional area, and moves forward in the plane perpendicular to visual axis with regards to the location of its center of volume.

Contraction of the ciliary muscle leads to changes in the three dimensional shape of the lens capsule as well as displacement of the optical center of the lens in relation to the overall optical center of the eye itself. This displacement alters the overall focal point of the eye allowing variability of focus from distance to near objects.

When accommodation is relaxed in the human eye, outward radial pull via tension in the suspensory ligaments (zonules) of the lens leads to an increase in the circular diameter of the space contained within the lens capsule in the plane approximately perpendicular to the visual axis and path of light from distant objects to the central retina of the eye. The act of accommodation causes the ciliary muscle of the eye to contract which releases tension in the suspensory lens ligaments resulting in reduced diameter of the lens in the visual plane and changes in the anterior and posterior surface curvatures of the lens as well as shifting of the optical center of the lens which result in increased convex diopteric power of the lens and consequently of the whole optical system of the eye allowing near objects to be focused on the retina.

The crystalline lens of the eye is normally flexible and is suspended within an elastic capsule. This capsule has to be penetrated to remove the cataractous lens.

The shape of the lens capsule and enclosed lens in its natural state depends on the interaction between the elastic nature of the capsule and also (a) the tension in the supporting zonules whose force and direction is varied by contraction of the ciliary muscle, (b) resistance and pressure from the vitreous humor against the posterior capsule surface, (c) forces on the anterior surface of the lens capsule from aqueous humor and iris, (d) gravity, and (e) resistance to deformity of the contents of the lens capsule, normally the crystalline lens.

One or more embodiments of the present disclosure utilize biometric changes occurring during CBA. The primary biometric changes utilized are reductions in the sulcus-to-sulcus diameter (SSD), the anterior chamber depth (ACD), the iris-ciliary process angle (ICPA), and the iris-zonula distance (IZD, or posterior chamber depth). Indirect or secondary biometric changes occurring during CBA that can be utilized in one or more embodiments of the present disclosure include reductions in the ciliary process-capsular bag distance (CP-CBD) decreases and the ciliary ring diameter (CRD).

Although there is considerable variability in the exact measured mean values for the various anatomical distance and angles compared in the relaxed and near accommodated state, this is not surprising given the normal anatomical variations between studied individuals as well as the variety of instruments and techniques used in different studies. Additionally, the resolution of the current technology is still sub optimal, as are agreements in precise location of landmarks. Because of the above-mentioned factors, comparison of the various studies shows a wide variability of the mean measured values in both the relaxed and near accommodated state, as well as large standard deviations in the mean difference values. This results in low confidence in the statistical significance of the mean differences in many of the studies. However, at least some embodiments of the present disclosure assume that there are some consistent and predictable variations in measured anatomical parameters during near accommodation including (a) a decrease in the SSD (sulcus-to-sulcus diameter) from approximately 11 mm to approximately 10.5 mm, (b) a decrease in the ICPA (Iris-ciliary process angle) from approximately 40 degrees to approximately 22 degrees, (c) a decrease in the ACA (anterior chamber angle) from approximately 32 degrees to approximately 28 degrees, (d) a decrease in the distance from the ciliary sulcus to the apex of the cornea caused by movement of the plane of the ciliary sulcus anteriorly along the visual axis, and (e) an increase in the diameter of the circular portion of the ciliary muscle. One or more embodiments of the present disclosure can use the above anatomical changes to mechanically link CBA to IOLA in a manner superior to the prior art.

With reference now to FIG. 1-6, an AIOL 10 can include a first lens 12, a first stanchion 14, a second lens 16, and a second stanchion 18. The first lens 12 can be configured for positioning in an eye and can have a first anterior side 20 and a first posterior side 22. The first anterior side 20 can face toward a pupil of the eye when the first lens 12 is positioned in the eye and the first posterior side 22 can face away from the pupil of the eye when the first lens 12 is positioned in the eye.

The first stanchion 14 can have a first distal end 24 connected to the first lens 12 and can extend away from the first lens 12 to a first base end 26. The first base end 26 can be configured for positioning within a capsular bag of the eye or on a ciliary sulcus/muscle of the eye whereby contraction of the ciliary sulcus/muscle during accommodation of the eye moves the first base end 26 towards an optic axis 28 of the eye. It is noted that positioning on the ciliary muscle of the eye does not mean that, in all embodiments of the present disclosure, the lens directly touches the ciliary muscle. Embodiments of the present disclosure include arrangement in which the lens does not directly touch the ciliary muscle. The optic axis of the eye and the optic axis of the AIOL 10 are collinear in FIGS. 1-6 and are jointly referenced at 28.

The second lens 16 can be configured for positioning in the eye with the first lens 12 and can have a second anterior side 30 and a second posterior side 32. The second anterior side 30 can face the first posterior side 22 when the first lens 12 and the second lens 16 are positioned in the eye and the second posterior side 32 can face into to the eye when the second lens 16 is positioned in the eye. It is noted that the perimeter of the second lens 16 is shown in dash-line in FIG. 1 not because the second lens 16 is fully hidden. The only portion of the second lens 16 not visible in FIG. 1 is the portion covered by the first lens 12. Dashed lines, having different dash properties, are used for various lenses so that the perimeters of all of the lenses can be seen together.

The second stanchion 18 can have a second distal end 34 connected to the second lens 16 and can extend away from the second lens 16 to a second base end 36. The second base end 36 can be configured for positioning within the capsular bag of the eye or on the ciliary sulcus/muscle of the eye whereby contraction of the ciliary sulcus/muscle during accommodation of the eye moves the second base end 36 towards the optic axis 28 of the eye.

Figure 2:
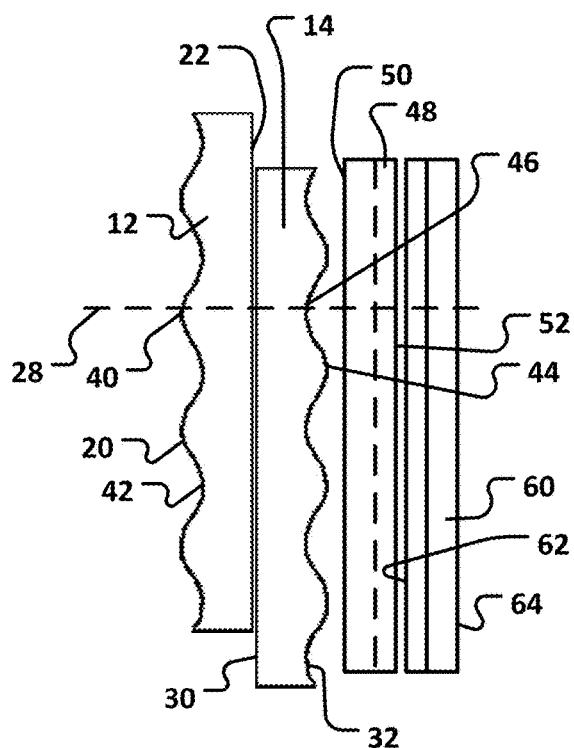
FIG. 2 is a first vertical cross-section through a portion of the accommodating intraocular lens assembly shown in FIG. 1.
Figure 3:
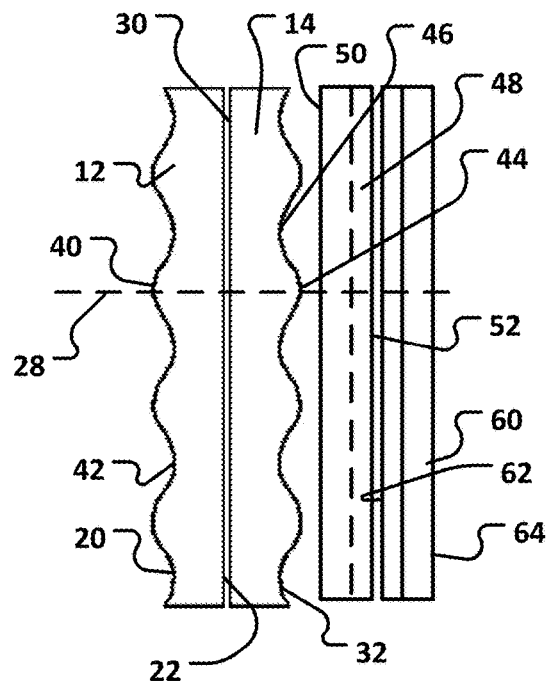
FIG. 3 is a second vertical cross-section through a portion of the accommodating intraocular lens assembly shown in FIG. 1.

The first lens 12 and the second lens 16 can move laterally relative to one another during contraction of the ciliary muscle in a vertically-extending plane containing the optic axis 28 of the eye and substantially centered in the eye. The lateral relative movement being lateral relative to the optic axis 28, in other words side-to-side relative to the optic axis 28 in contrast to along the optic axis 28. In FIG. 1, the vertically-extending plane is referenced by view lines 38. FIGS. 2 and 3 are views of portions of cross-sections of the lenses 12, 16 in the vertically-extending plane 38. FIG. 2 shows an exemplary spatial relationship between the lenses 12, 16 when the ciliary muscle is relaxed. FIG. 3 shows an exemplary spatial relationship between the lenses 12, 16 when the ciliary muscle is contracted. Cooperatively, FIGS. 2 and 3 show relative movement of the lenses 12, 16 that is lateral relative to the optic axis 28.

Figure 4:
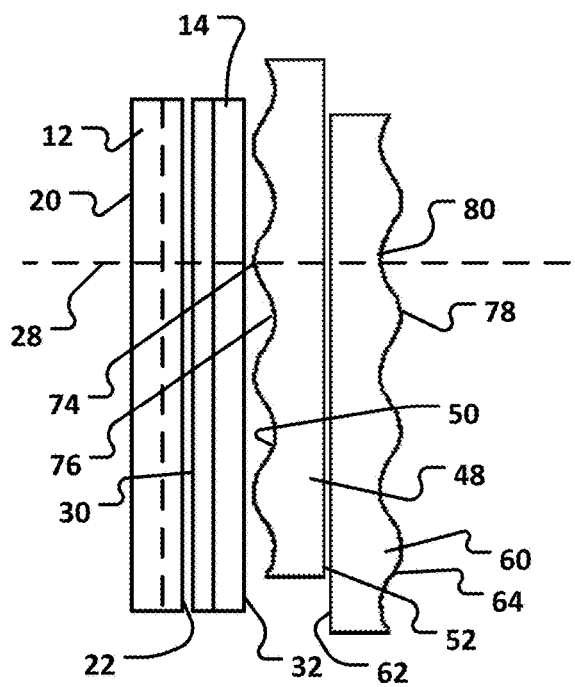
FIG. 4 is a first horizontal cross-section through a portion of the accommodating intraocular lens assembly shown in FIG. 1.
Figure 5:
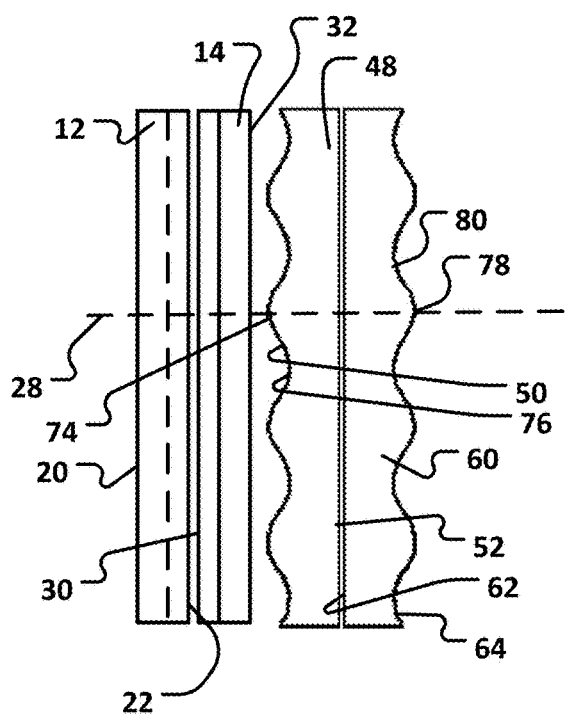
FIG. 5 is a second horizontal cross-section through a portion of the accommodating intraocular lens assembly shown in FIG. 1.

It is noted that, in one or more embodiments of the present disclosure, the first posterior side 22 of the first lens 12 and the second anterior side 30 of the second lens 16 can be in contact with one another and slide across one another during contraction of the ciliary muscle. In one or more other embodiments of the present disclosure, the first posterior side 22 of the first lens 12 and the second anterior side 30 of the second lens 16 can be in spaced from one another and can be guided in relative movement by mating tongue and groove joints, mating slots, or other structures. FIGS. 2-5 show the surfaces 22, 30 spaced from one another and FIG. 5 shows the surfaces 22, 30 in contact with one another.

In the exemplary embodiment, the first anterior side 20 of the first lens 12 and the second posterior side 32 of the second lens 16 are mirrored in shape with respect to one another in the vertically-extending plane 38. By way of example and not limitation, the first anterior side 20 of the first lens 12 and the second posterior side 32 of the second lens 16 each define respective, wavy surfaces in the vertically-extending plane 38. Each respective wavy surface including at least one crest and at least one trough. An exemplary crest of the first anterior side 20 of the first lens 12 is referenced at 40 and a trough is referenced at 42 in FIGS. 2 and 3. An exemplary crest of the second posterior side 32 of the second lens 16 is referenced at 44 and a trough is referenced at 46 in FIGS. 2 and 3.

As shown in FIGS. 2 and 3, in the exemplary embodiment, the first lens 12, the first stanchion 14, the second lens 16, and the second stanchion 18 are configured such that when the ciliary muscle is relaxed the crest 40 of the wavy surface of the first anterior side 20 of the first lens 12 is substantially aligned in the vertically-extending plane 38 with the trough 46 of the wavy surface of the second posterior side 32 of the second lens 16. Thus, the profiles of the dual lenses 12, 16 cooperate to produce no net additional optical power through the central pupillary visual axis. The optical undulations in one surface are neutralized by corresponding undulations in the other optic.

Conversely, when the ciliary muscle is contracted, the crest 40 of the wavy surface of the first anterior side 20 of the first lens 12 is substantially aligned in the vertically-extending plane 38 with the crest 44 of the wavy surface of the second posterior side 32 of the second lens 16. Thus, the profiles of the dual lenses 12, 16 cooperate to produce increased converging power in the central pupillary visual axis. In other embodiments, spherical power change could be maximized in the center of the lenses 12, 16 and controllably reduced in the periphery to achieve any increase in converging power by designing the configuration of the optical undulations. For example, if the undulations were maximum only in the center of the optical elements (parallel to the direction of their translation), then the increased cylindrical power would be maximum centrally and could be modulated to be only spherical for practical purposes. Other manipulations of the undulations can be made such as curve of the wave front of the undulations, frequency and amplitude. Higher level patterns of undulations could be superimposed on lower level undulation patterns to achieve the desired optical result for the optimal degree of translation achievable.

The exemplary AIOL 10 also includes a third lens 48 configured for positioning in the eye and having a third anterior side 50 and a third posterior side 52. The third anterior side 50 can face toward the pupil of the eye when the third lens 48 is positioned in the eye. The third posterior side 52 can face away from a pupil of the eye when the third lens 48 is positioned in the eye. It is noted that the perimeter of the third lens 48 is shown in dash-line in FIG. 1 not because the third lens 48 is fully hidden. The only portion of the third lens 48 not visible in FIG. 1 is the portion covered by the first lens 12 and the second lens 16. Dashed lines, having different dash properties, are used for various lenses so that the perimeters of all of the lenses can be seen together.

The exemplary AIOL 10 also includes a third stanchion 54 having a third distal end 56 connected to the third lens 48. The third distal end 56 can extend away from the third lens 48 to a third base end 58. The third base end 58 can be configured for positioning within a capsular bag of the eye or on a ciliary muscle of the eye whereby contraction of the ciliary muscle during accommodation of the eye moves the third base end 58 towards an optic axis 28 of the eye.

The exemplary AIOL 10 also includes a fourth lens 60 configured for positioning in the eye with the third lens 48. The fourth lens 60 can have a fourth anterior side 62 and a fourth posterior side 64. The fourth anterior side 62 can face the third posterior side 52 when the third lens 48 and the fourth lens 60 are positioned in the eye and the fourth posterior side 64 can face into to the eye when the fourth lens 60 is positioned in the eye.

The exemplary AIOL 10 also includes a fourth stanchion 66 having a fourth distal end 68 connected to the fourth lens 60. The fourth stanchion 66 can extend away from the fourth lens 60 to a fourth base end 70. The fourth base end 70 can be configured for positioning within the capsular bag of the eye or on the ciliary muscle of the eye whereby contraction of the ciliary muscle during accommodation of the eye moves the fourth base end 70 towards the optic axis 28 of the eye.

In the exemplary embodiment, the third lens 48 and the fourth lens 60 can move laterally relative to one another during contraction of the ciliary muscle in a horizontally-extending plane containing the optic axis 28 of the eye and perpendicular to the vertically-extending plane 38. In FIG. 1, the horizontally-extending plane is referenced by view lines 72. FIGS. 4 and 5 are views of portions of cross-sections of the lenses 48, 60 in the horizontally-extending plane 72.

The third anterior side 50 of the third lens 48 can face the second posterior side 32 of the second lens 16. In the exemplary embodiment, when the first lens 12 and the second lens 16 and the third lens 48 and the fourth lens 60 are positioned in the eye, the first stanchion 14 and the second stanchion 18 are spaced substantially one hundred and eighty degrees from one another about the optic axis 28. The third stanchion 54 and the fourth stanchion 66 can be spaced substantially one hundred and eighty degrees from one another about the optic axis 28. The first stanchion 14 and the third stanchion 54 can be spaced substantially ninety degrees from one another about the optic axis 28.

In the exemplary embodiment, the third anterior side 50 defines a third wavy surface in the horizontally-extending plane 72. The third wavy surface including at least one third crest and at least one third trough. An exemplary crest of the third anterior side 50 of the third lens 48 is referenced at 74 and a trough is referenced at 76 in FIGS. 4 and 5. The fourth posterior side 64 of the fourth lens 60 can define a fourth wavy surface in the horizontally-extending plane 72 including at least one fourth crest and at least one fourth trough. An exemplary crest of the fourth posterior side 64 of the fourth lens 60 is referenced at 78 and a trough is referenced at 80 in FIGS. 4 and 5.

The third lens 48, the third stanchion 54, the fourth lens 60, and the fourth stanchion 66 are configured such that when the ciliary muscle is relaxed the crest 74 of the third wavy surface of the third anterior side 50 of the third lens 48 is substantially aligned in the horizontally-extending plane 72 with the fourth trough 80 of the fourth wavy surface of the fourth posterior side 64 of the fourth lens 60. When the ciliary muscle is contracted, the crest 74 of the third wavy surface of the third anterior side 50 of the third lens 48 is substantially aligned in the horizontally-extending plane 72 with the fourth crest 78 of the fourth wavy surface of the fourth posterior side 64 of the fourth lens 60.

Figure 6:
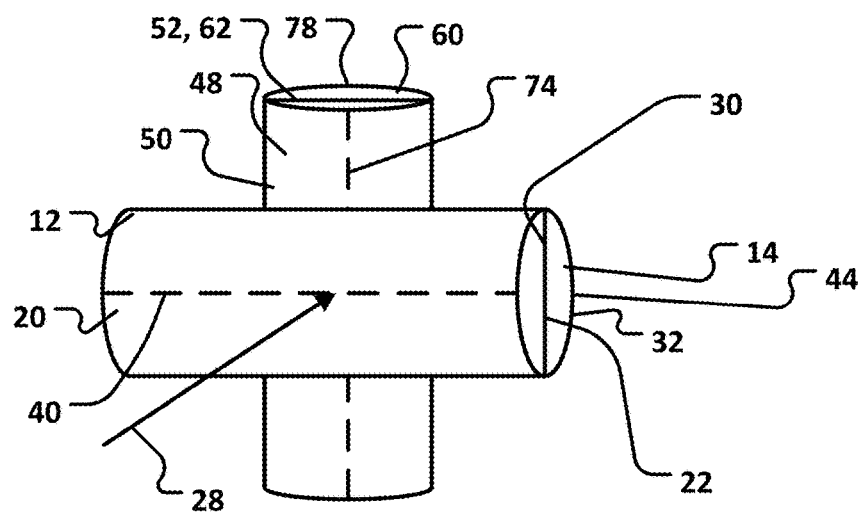
FIG. 6 is a schematic representation of alignment of the lenses of the accommodating intraocular lens assembly shown in FIG. 1.

As best shown in FIG. 6, when the ciliary muscle is contracted, the first crest 40 of the first wavy surface of the first anterior side 20 of the first lens 12, the second crest 44 of the second wavy surface of the second posterior side 32 of the second lens 16, the third crest 74 of the third wavy surface of the third anterior side 50 of the third lens 48, and the fourth crest 78 of the fourth wavy surface of the fourth posterior side 64 of the fourth lens 60 are substantially centered on the optic axis 28 of the eye. The lenses 12, 16, 48, 60 thus form double cylinders at a right angle to one another. This arrangement forms a Stokes' lens in which two cylinders or equal power are created with their axes perpendicular resulting in an increased spherical power converging lens.

Figure 7:
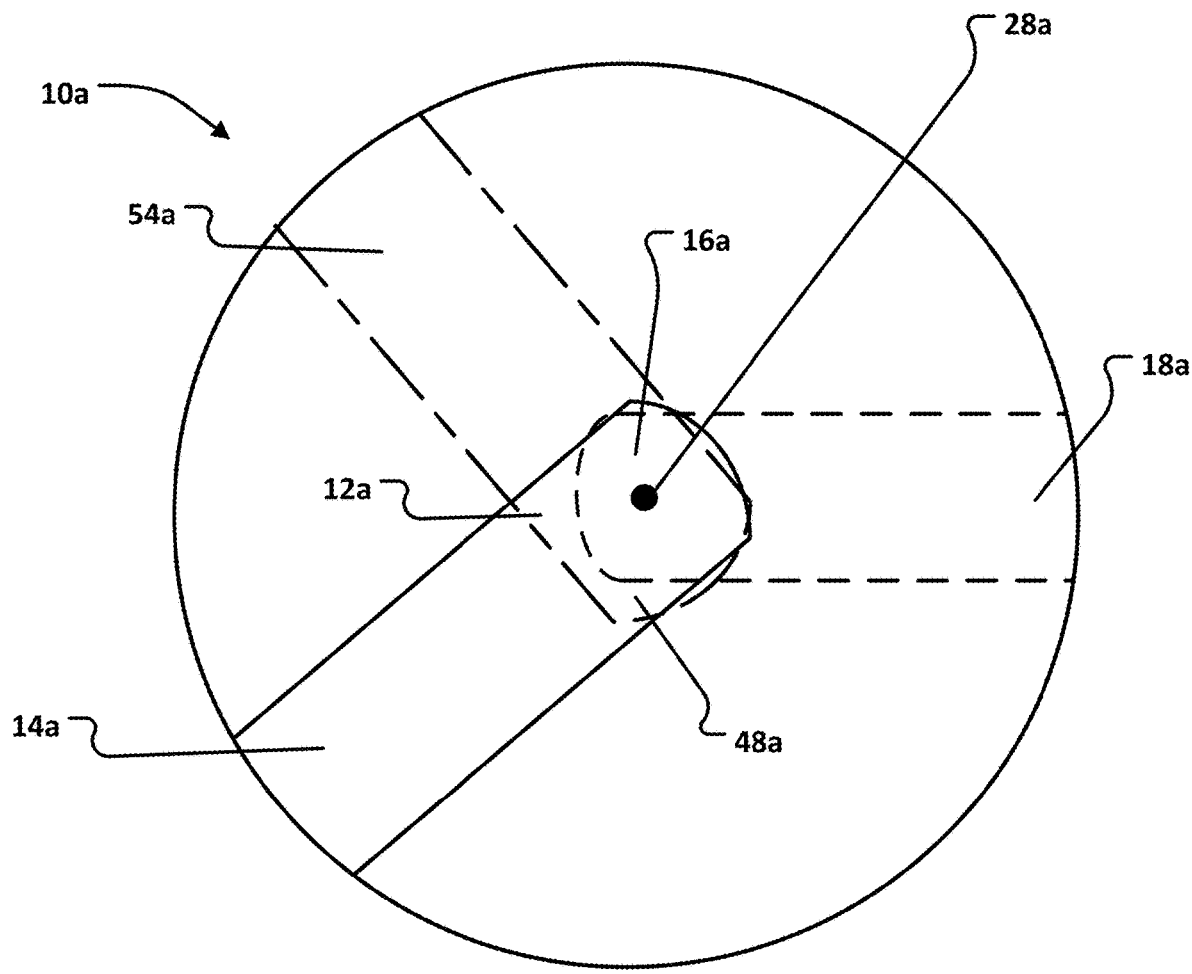
FIG. 7 is a schematic front view of an accommodating intraocular lens assembly according to another exemplary embodiment of the present disclosure.

With reference now to FIG. 7, in another embodiment of the present disclosure, an AIOL 10*aa* can include can include a first lens 12*a*, a first stanchion 14*a*, a second lens 16*a*, a second stanchion 18*a*, a third lens 48*a*, and a third stanchion 54*a*. The optic axis of the eye and the optic axis of the AIOL 10*a* are collinear in FIG. 7 and are jointly referenced at 28*a*. The first stanchion 14*a*, the second stanchion 18*a*, and the third stanchion 54*a* are evenly spaced from one another about the optic axis 28*a*. The stanchions 14*a*, 18*a*, 54*a* supporting the optics 12*a*, 16*a*, 48*a* would be configured to create inwards movements of the optics 12*a*, 16*a*, 48*a* towards the center of the visual axis 28*a* in addition to anterior and posterior movement relative to each other. Such centripetal movement could be achieved by modulating the rigidity and elasticity of the stanchions 14a, 18a, 54a. The three optics 12a, 16a, 48a can cumulatively have overall power that varies as a degree of overlap varies according to ciliary muscle action.

With reference now to FIGS. 8 and 9, an AIOL according to an embodiment of the present disclosure can include a first lens 12b or a second lens 16b that defines a Fresnel array. In FIGS. 8 and 9, the first lens 12b defines a first Fresnel array including a first plurality of sub-lenses such as sub-lenses 82b, 182b, 282b, 382b oriented in the vertically-extending plane. The second lens 16b defines a second Fresnel array including a second plurality of sub-lenses such as sub-lenses 84b, 184b, 284b, 384b oriented in the vertically-extending plane.

The first plurality of sub-lenses 82b, 182b, 282b, 382b and the second plurality of sub-lenses 84b, 184b, 284b, 384b include sub-elements having different levels of additive optical power. Exemplary FIG. 8 can correspond to the ciliary muscle at rest and the Fresnel lens arrays can be utilized in a distance gaze with corresponding additive optical powers of each lens pair. For example, vision is assisted by the optical power provided by sub-lens combinations 82b-184b, 182b-284b, and 282b-384b. Exemplary FIG. 9 can correspond to the ciliary muscle contracted, after relative translation between the lenses 12b, 16b. The new lens system can have significantly different power achieved by minimum relative movement. vision is assisted by the optical power provided by sub-lens combinations 82b-84b, 182b-184b, 282b-284b. The sub-lens combinations 82b-84b, 182b-184b, 282b-284b define greater optical power than the sub-lens combinations 82b-184b, 182b-284b, and 282b-384b.

In one or more embodiments of the present disclosure, an AIOL can include a lens having an optical metasurface. Optical metasurfaces include sub-wavelength, patterned layers that can interact with light by altering the light properties over a sub-wavelength thickness. An embodiment of the present disclosure can include a metalenses fabricated from wide bandgap transparent materials, such as titanium oxide and gallium nitride. The utilization of a metasurface can reduces the volume of the AIOL. Further, the AIOL can be fabricated with semiconductor fabrication technologies, with the potential to be mass-produced at a low unit cost.

With reference now to FIGS. 10-13, in another exemplary embodiment of the present disclosure, an AIOL 10c includes a first lens 12c, a first stanchion 14c, a second lens 16c, and a second stanchion 18c. The first lens 12c can be configured for positioning in an eye and can have a first anterior side 20c and a first posterior side (not visible but on the opposite side of the first lens 12c relative to the side 20c). The first anterior side 20c can face toward a pupil of the eye when the first lens 12c is positioned in the eye and the first posterior side can face away from a pupil of the eye when the first lens 12c is positioned in the eye.

Figure 10:
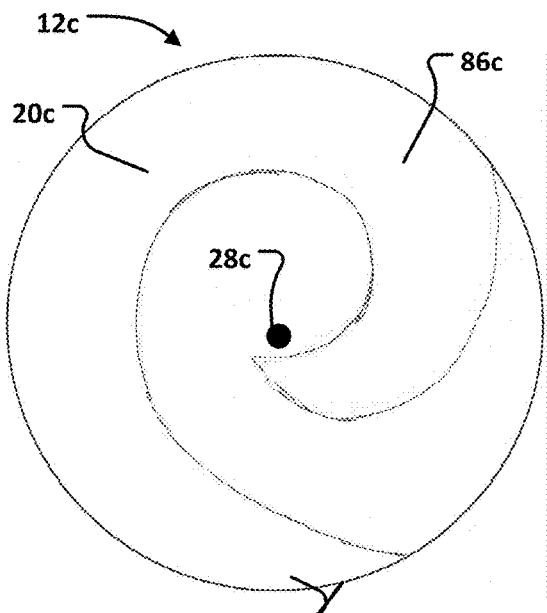
FIG. 10 is a front view a first lens of an accommodating intraocular lens assembly according to another exemplary embodiment of the present disclosure.
Figure 12:
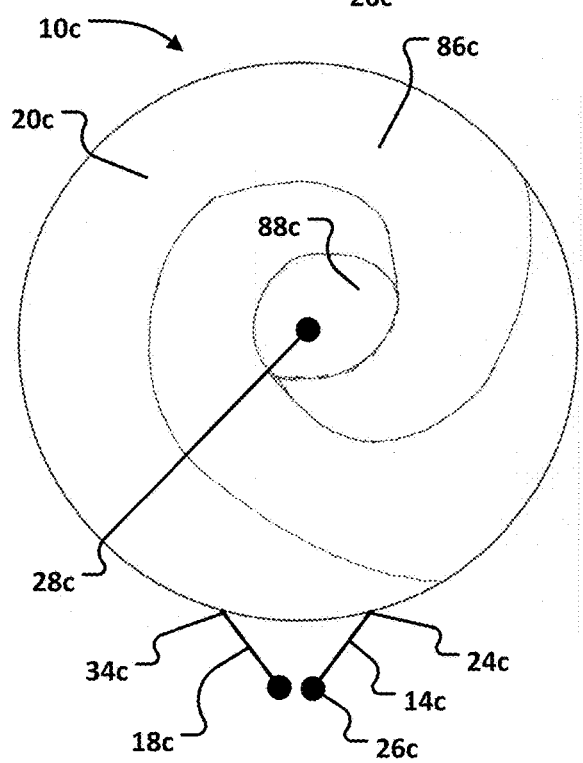
FIG. 12 is a first front view a first and second lens of the accommodating intraocular lens assembly shown partially in FIGS. 10 and 11, the first and second lenses overlaid with respect to one another.

The first stanchion 14c can have a first distal end 24c connected to the first lens 12c and can extend away from the first lens 12c to a first base end 26c. The first base end 26c can be configured for positioning within a capsular bag of the eye or on a ciliary muscle of the eye whereby contraction of the ciliary muscle during accommodation of the eye moves the first base end 26c towards an optic axis 28c of the eye. An axis extending between the first base end 26c and the first distal end 24c does not intersect the optic axis 28c of the eye, as can be seen in FIGS. 10 and 12. While only one first stanchion 14c is shown, it is noted that the AIOL 10c can include a plurality of first stanchions 14c arranged around the periphery of the first lens 12c. This point is also applicable to other disclosed embodiments.

The second lens 16c can be configured for positioning in the eye with the first lens 12c and can have a second anterior side 30c and a second posterior side (not visible but on the opposite side of the second lens 16c relative to the side 30c). The second anterior side 30c can face the first posterior side when the first lens 12c and the second lens 16c are positioned in the eye. The second posterior side can face into to the eye when the second lens 16c is positioned in the eye.

Figure 11:
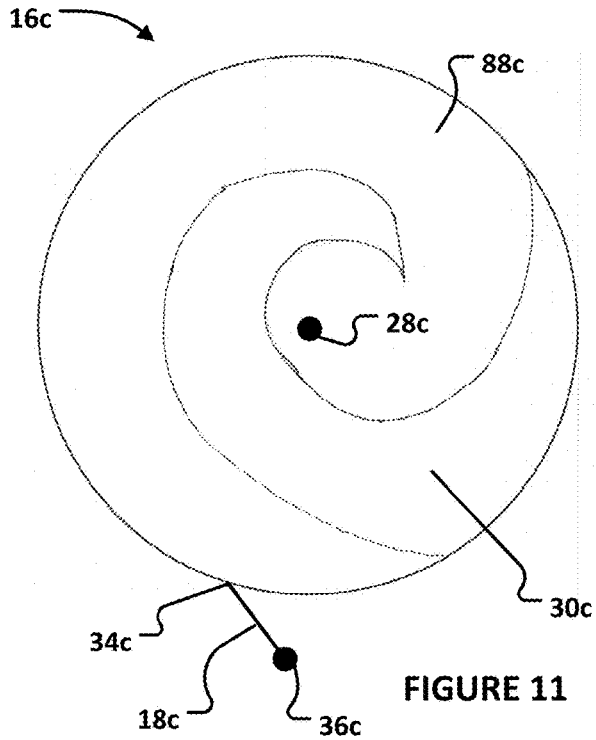
FIG. 11 is a front view a second lens of the accommodating intraocular lens assembly shown partially in FIG. 10.

The second stanchion 18c can have a second distal end 34c connected to the second lens 16c and can extend away from the second lens 16c to a second base end 36c. The second base end 36c can be configured for positioning within the capsular bag of the eye or on the ciliary muscle of the eye whereby contraction of the ciliary muscle during accommodation of the eye moves the second base end 36c towards the optic axis 28c of the eye. An axis extending between the second base end 36c and the second distal end 34c does not intersect the optic axis 28c of the eye, as shown in FIGS. 11 and 12. While only one second stanchion 18c is shown, it is noted that the AIOL 10c can include a plurality of second stanchions 18c arranged around the periphery of the second lens 16c.

The first stanchion 14c and the second stanchion 18c are configured such that the first lens 12c and the second lens 16c rotate relative to one another about the optic axis 28c of the eye during contraction of the ciliary muscle. When the base ends 26c, 36c are urged toward the axis 28c, the stanchions 14c, 18c do not bend and thereby cause rotation of each lens 12c, 16c in opposite directions.

The first lens 12c defines a spiral refractive variation pattern in the area referenced at 86c in FIG. 10. The second lens 16c also defines a spiral refractive variation pattern, in the area referenced at 88c in FIG. 11. When the spiral refractive variations 86c, 88c overlap one another, such as shown in FIG. 12, the spiral refractive variation 88c can be mostly neutralized by the spiral refractive variation 86c. FIG. 12 shows spiral refractive variation portions 86c, 88c superimposed resulting in a neutral optical condition except for the center which is responsible for minimal refraction. As shown in FIG. 12, a portion of the spiral refractive variation 88c remains uncovered.

Figure 13:
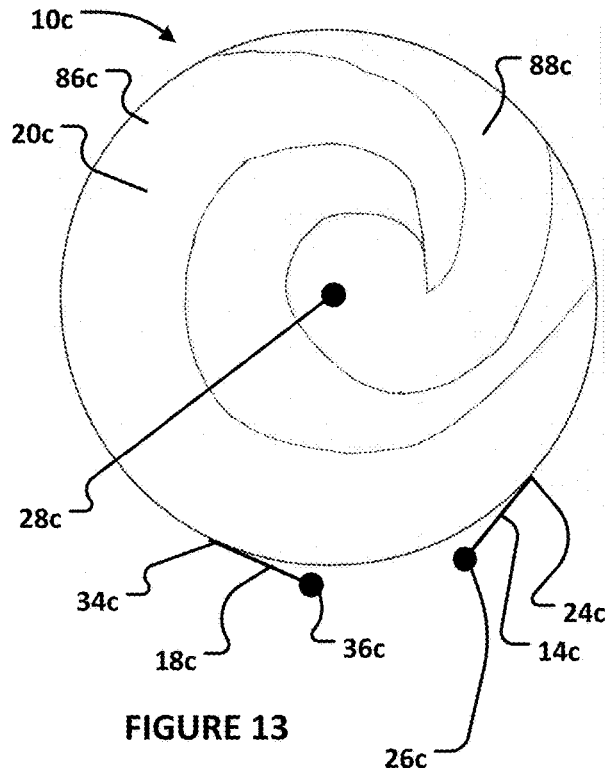
FIG. 13 is a second front view a first and second lens of the accommodating intraocular lens assembly shown partially in FIGS. 10 and 11, the first and second lenses overlaid with respect to one another.

A small degree of relative rotation changes the extent of overlap. FIG. 13 shows relative rotation exposes excess converging power in the central and peripheral regions. It is noted that in FIG. 13 the lens 16c is shown in the same position as FIG. 11 and all of the relative rotation has been applied to lens 12c. A larger portion of the spiral refractive variation 88c around the axis 28c becomes exposes, increasing central optical power to a larger degree. Also, a peripheral portion of the spiral refractive variation 88c becomes exposed.

Figure 14:
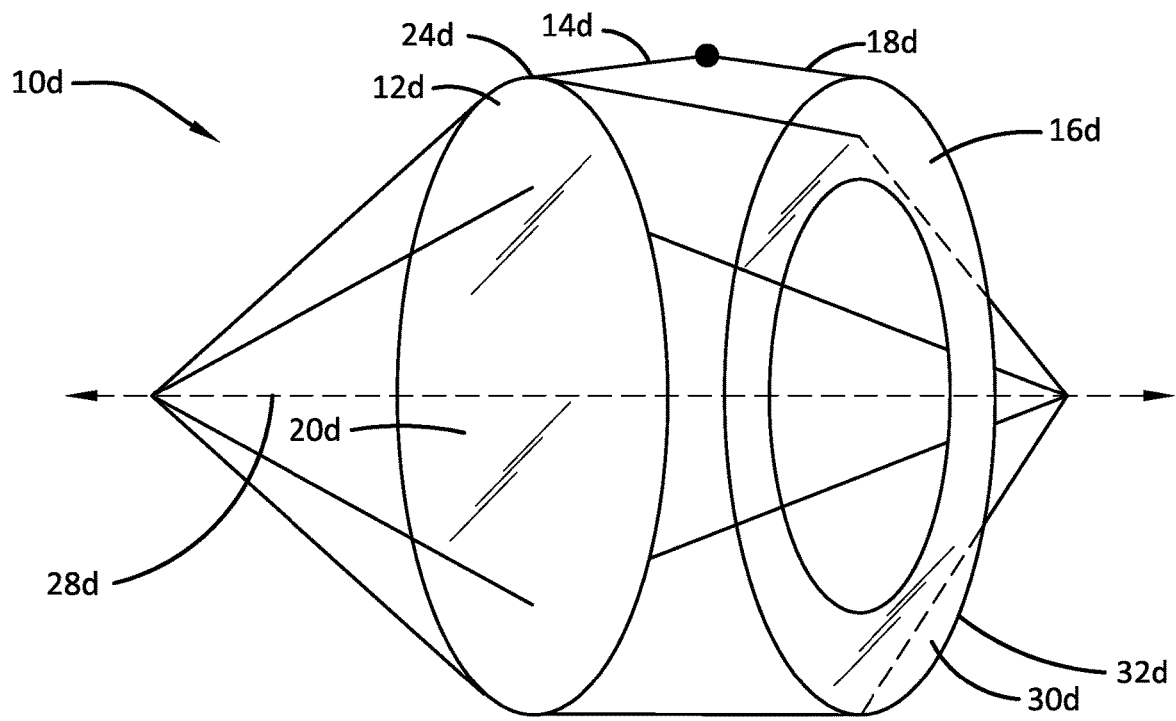
FIG. 14 is a first isometric view, generally from the side, of an accommodating intraocular lens assembly according to another exemplary embodiment of the present disclosure.
Figure 15:
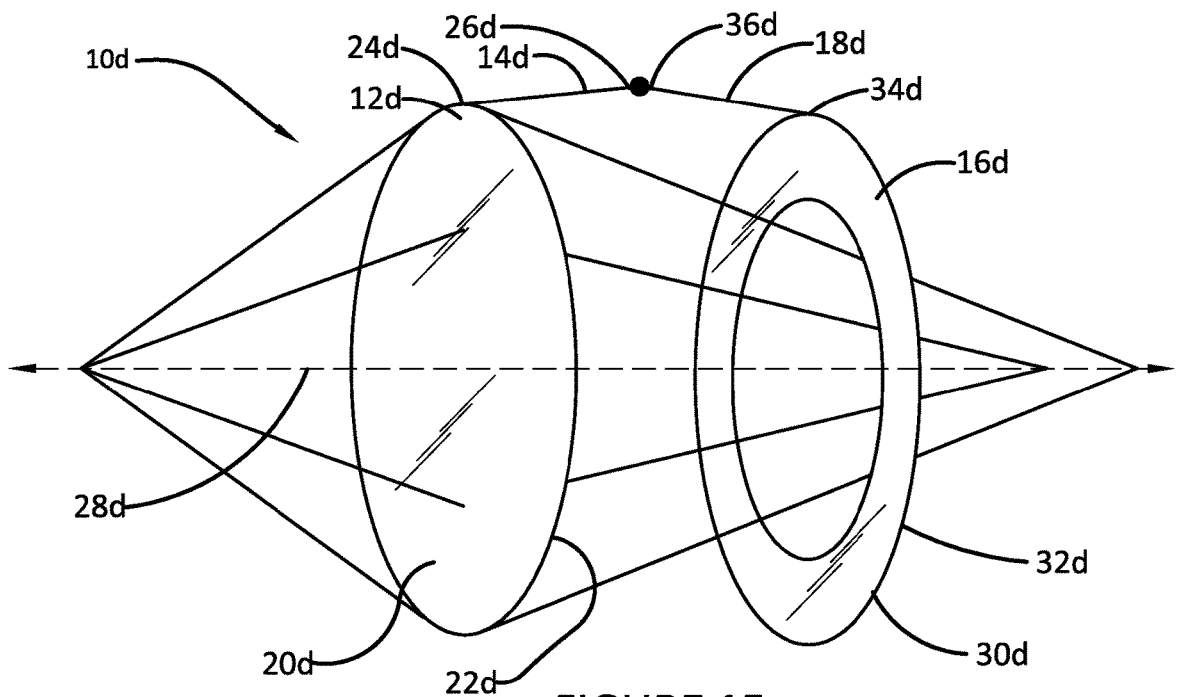
FIG. 15 is a second isometric view, generally from the side, of the accommodating intraocular lens assembly shown in FIG. 14.

With reference now to FIGS. 14 and 15, in another exemplary embodiment of the present disclosure, an AIOL 10d includes a first lens 12d, a first stanchion 14d, a second lens 16d, and a second stanchion 18d. The first lens 12d can be configured for positioning in an eye and can have a first anterior side 20d and a first posterior side 22d. The first anterior side 20d can face toward a pupil of the eye when the first lens 12d is positioned in the eye and the first posterior side 22d can face away from the pupil of the eye when the first lens 12d is positioned in the eye.

The first stanchion 14d can have a first distal end 24d connected to the first lens 12d and can extend away from the first lens 12d to a first base end 26d. The first base end 26d can be configured for positioning within a capsular bag of the eye or on a ciliary muscle of the eye whereby contraction of the ciliary muscle during accommodation of the eye moves the first lens 12d along an optic axis 28d of the eye.

The second lens 16d can be configured for positioning in the eye with the first lens 12d. The second lens 16d can have a second anterior side 30d and a second posterior side 32d. The second anterior side 30d can face the first posterior side 22d when the first lens 12d and the second lens 16d are positioned in the eye and the second posterior side 32d can face into to the eye when the second lens 16d is positioned in the eye.

The second stanchion 18d can have a second distal end 34d connected to the second lens 16d and can extend away from the second lens 16d to a second base end 36d. The second base end 36d can be configured for positioning within the capsular bag of the eye or on the ciliary muscle of the eye whereby contraction of the ciliary muscle during accommodation of the eye moves the second lens 16d along the optic axis 28d of the eye.

A shape of the first lens 12d is an aperture-less disc and a shape of the second lens 16d is a disc with a centered aperture. This dual optic AIOL 10d defines an aspheric optical design so that convex (converging) power is weighted either in the periphery or the center of one optic. Relative movement of optics 12d, 16d results in a varying portion of the optic furthest from the Iris being included in the optical path of light focused by the cornea through the intraocular lens. When the separation between the optics 12d, 16d is increased, the periphery of the optic furthest from the Iris is relatively excluded from the optical path of light focused by the eye. Therefore, if converging power is weighted in the periphery of the optic furthest from the Iris, decreased separation of the optics 12d, 16d would result in more converging power being included in the path of light and the focal point of the eye being bought closer. Therefore, during near accommodation, the overall focal point of the eye is biased towards near objects. The utility of such a mechanism would be important in dual (or multiple) optic intraocular lens designs where decreased separation of the optical elements during near accommodation is desirable in contrast to multiple optic intraocular lens designs that rely on increased converging power achieved by increase separation of positive power optical elements. This benefit may be useful when incorporating nano lenses for intraocular lens implants. In the alternative, the central portion of the optical element furthest from the Iris may be preferentially weighted with converging power so that increased separation of the optical elements results in an overall increase in converging power by excluding the annular periphery of the second optic, said mechanism augmenting other methods of near focusing during accommodation by the intraocular lens.

Figures 16, 17:
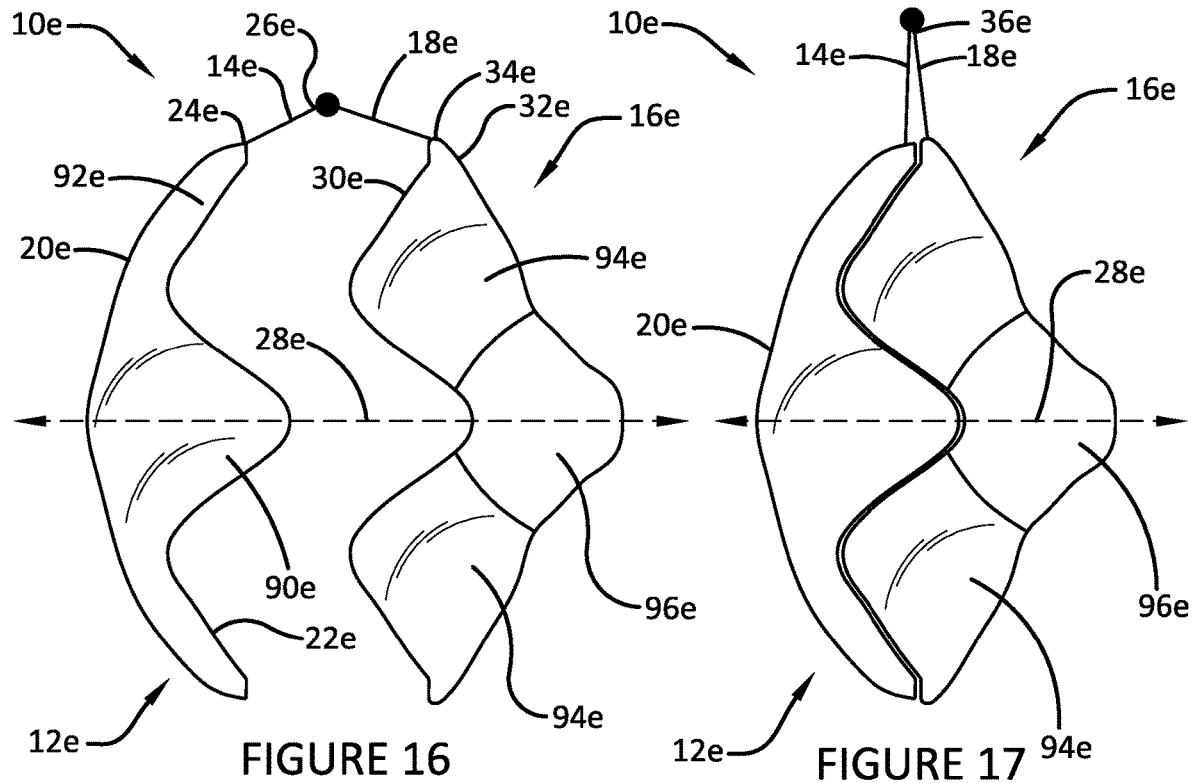
FIG. 16 is a first side view of an accommodating intraocular lens assembly according to another exemplary embodiment of the present disclosure.
FIG. 17 is a second side view of the accommodating intraocular lens assembly shown in FIG. 16.
Figure 18:
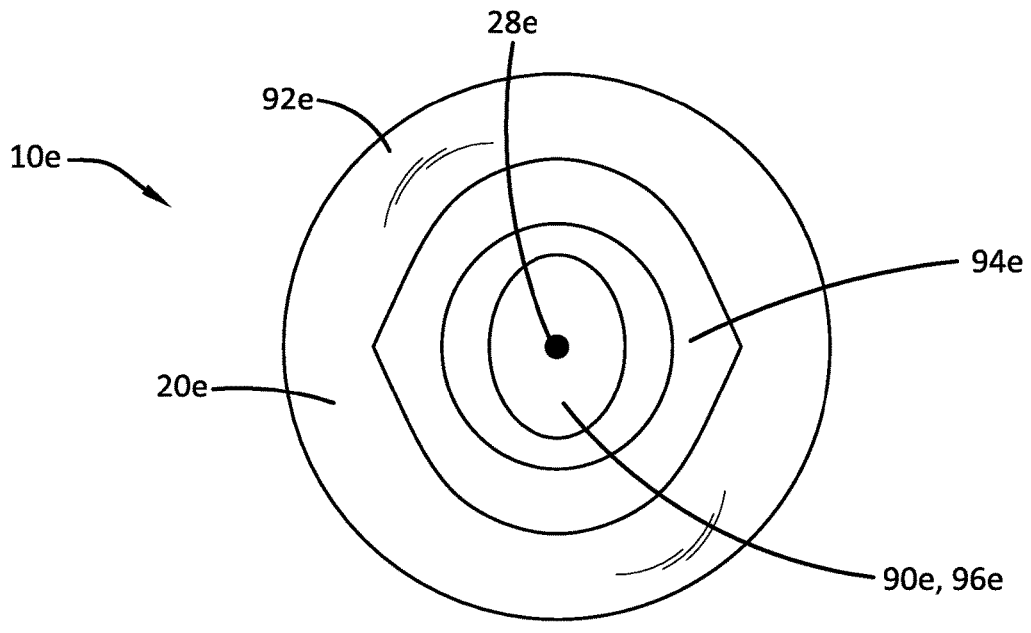
FIG. 18 is a front view of the accommodating intraocular lens assembly shown in FIG. 17.

With reference now to FIGS. 16-18, in another exemplary embodiment of the present disclosure, an AIOL 10e includes a first lens 12e, a first stanchion 14e, a second lens 16e, and a second stanchion 18e. The first lens 12e can be configured for positioning in an eye and can have a first anterior side 20e and a first posterior side 22e. The first anterior side 20e can face toward a pupil of the eye when the first lens 12e is positioned in the eye and the first posterior side 22e can face away from a pupil of the eye when the first lens 12e is positioned in the eye.

The first stanchion 14e can have a first distal end 24e connected to the first lens 12e and can extend away from the first lens 12e to a first base end 26e. The first base end 26e can be configured for positioning within a capsular bag of the eye or on a ciliary muscle of the eye whereby contraction of the ciliary muscle during accommodation of the eye moves the first lens 12e along an optic axis 28e of the eye.

The second lens 16e can be configured for positioning in the eye with the first lens 12e and can have a second anterior side 30e and a second posterior side 32e. The second anterior side 30e can face the first posterior side 22e when the first lens 12e and the second lens 16e are positioned in the eye and the second posterior side 32e can face into to the eye when the second lens 16e is positioned in the eye.

The second stanchion 18e can have a second distal end 34e connected to the second lens 16e and can extend away from the second lens 16e to a second base end 36e. The second base end 36e can be configured for positioning within the capsular bag of the eye or on the ciliary muscle of the eye whereby contraction of the ciliary muscle during accommodation of the eye moves the second lens 16e along the optic axis 28e of the eye.

The first posterior side 22e defines a first surface and the second anterior side 30e defines a second surface. The first surface and the second surface are mirrored in shape with respect to one another and interlock when the first lens 12e and the second lens 16e move due to contraction of the ciliary muscle during accommodation, as shown in FIG. 17. AIOL 10e is a roughly spherical dual optic IOL in cross section. The lens 12e includes a converging element portion 90e and a diverging element portion 92e. The lens 16e includes a portion 94e that converges peripherally and a central portion 96e that is converging. Refractive indices and optical powers can be selected to achieve desirable optical changes on relative separation of the lenses 12e and 16e.

Figure 19:
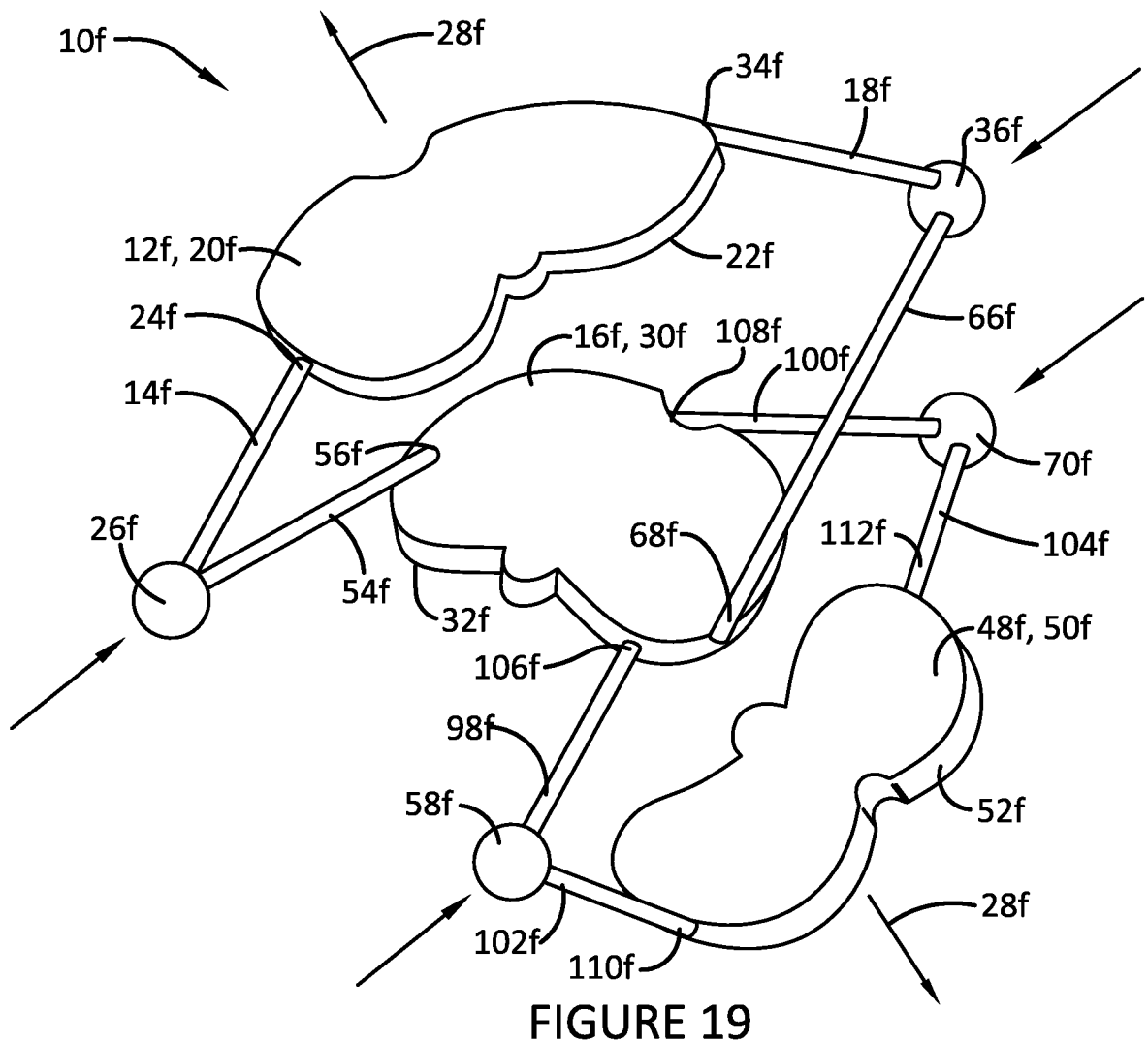
FIG. 19 is an isometric view, generally from the side, of an accommodating intraocular lens assembly according to another exemplary embodiment of the present disclosure.
Figure 20:
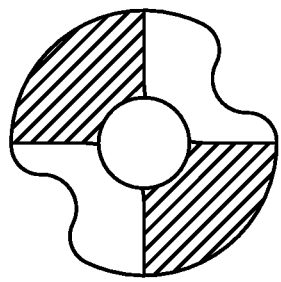
FIG. 20 is a first front view of the accommodating intraocular lens assembly shown in FIG. 19.
Figure 21:
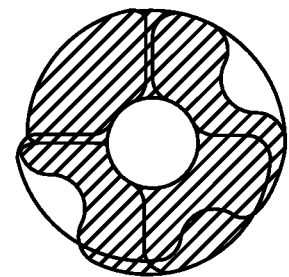
FIG. 21 is a second front view of the accommodating intraocular lens assembly shown in FIG. 19.

With reference now to FIGS. 19-21, in another exemplary embodiment of the present disclosure, an AIOL 10f includes a first lens 12f, a first stanchion 14f, a second stanchion 18f, a second lens 16f, a third stanchion 54f, a fourth stanchion 66f, a fifth stanchion 98f, a sixth stanchion 100f, a third lens 48f, a seventh stanchion 102f, and an eighth stanchion 104f. The first lens 12f can be configured for positioning in an eye and can have a first anterior side 20f and a first posterior side 22f. The first anterior side 20f can face toward a pupil of the eye when the first lens 12f is positioned in the eye and the first posterior side 22f can face away from the pupil of the eye when the first lens 12f is positioned in the eye.

The first stanchion 14f can have a first distal end 24f connected to the first lens 12f and can extend away from the first lens 12f to a first base end 26f. The second stanchion 18f can have a second distal end 34f connected to the first lens 12f and can extend away from the first lens 12f to a second base end 36f.

The second lens 16f can be configured for positioning in the eye with the first lens 12f and can have a second anterior side 30f and a second posterior side 32f. The second anterior side 30f can face the first posterior side 22f when the first lens 12f and the second lens 16f are positioned in the eye. The second posterior side 32f can face away from the pupil of the eye when the second lens 16f is positioned in the eye.

The third stanchion 54f having a third distal end 56f connected to the second lens 16f and can extend away from the second lens 16f to the first base end 26f. The first stanchion 14f and the third stanchion 54f can merge at the first base end 26f. The fourth stanchion 66f can have a fourth distal end 68f connected to the second lens 16f and can extend away from the second lens 16f to the second base end 36f. The second stanchion 18f and the fourth stanchion 66f can merge at the second base end 36f. The first base end 26f and the second base end 36f can be configured for positioning within the capsular bag of the eye or on the ciliary muscle of the eye whereby contraction of the ciliary muscle during accommodation of the eye moves the first lens 12*f* along the optic axis 28*f* of the eye.

The fifth stanchion 98*f* can have a fifth distal end 106*f* connected to the second lens 16*f* and can extend away from the second lens 16*f* to a third base end 58*f*. The sixth stanchion 100*f* can have a sixth distal end 108*f* connected to the second lens 16*f* and can extend away from the second lens 16*f* to a fourth base end 70*f*.

The third lens 48*f* can be configured for positioning in the eye with the first lens 12*f* and the second lens 16*f*. The third lens 48*f* can have a third anterior side 50*f* and a third posterior side 52*f*. The third anterior side 50*f* can face the second posterior side 32*f* when the second lens 16*f* and the third lens 48*f* are positioned in the eye. The third posterior side 52*f* can face away from the pupil of the eye when the third lens 48*f* is positioned in the eye.

The seventh stanchion 102*f* can have a seventh distal end 110*f* connected to the third lens 48*f* and can extend away from the third lens 48*f* to the third base end 58*f*. The fifth stanchion 98*f* and the seventh stanchion 102*f* can merge at the third base end 58*f*. The eighth stanchion 104*f* can have an eighth distal end 112*f* connected to the third lens 48*f* and can extend away from the third lens 48*f* to the fourth base end 70*f*. The sixth stanchion 100*f* and the eighth stanchion 104*f* can merge at the fourth base end 70*f*.

The third base end 58*f* and the fourth base end 70*f* can be configured for positioning within the capsular bag of the eye or on the ciliary muscle of the eye whereby contraction of the ciliary muscle during accommodation of the eye moves the third lens 48*f* along the optic axis 28*f* of the eye.

The lenses 12*f*, 16*f*, and 48*f* are shaped so that they can be inserted through an incision less than their respective optical diameters without the need for folding. Further, lenses 12*f*, 16*f*, and 48*f* can be wound around the optic axis 28*f* to be coiled in a compact manner. This design also lends itself well to the Alvarez principal modification. Contraction of the ciliary muscle can also induce rotation in one or more of the lenses 12*f*, 16*f*, and 48*f* to achieve variable spherical power via complimentary arrangement of optical zones. FIG. 20 shows an arrangement when the ciliary muscle is relaxed. The gray and black areas represent portions of overlap of all three lenses 12*f*, 16*f*, and 48*f*. FIG. 21 shows an arrangement when the ciliary muscle is contracted. The gray and black areas again represent portions of overlap of all three lenses 12*f*, 16*f*, and 48*f*.

Figure 22:
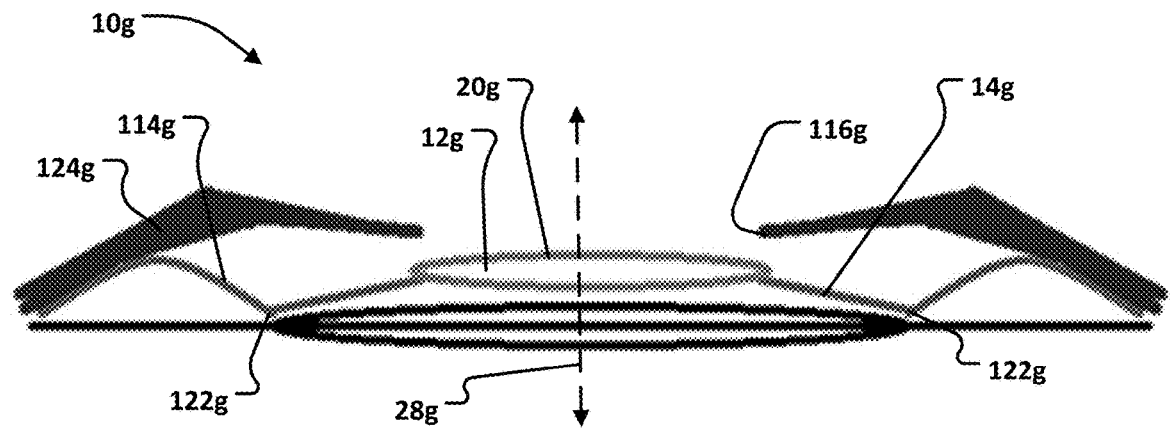
FIG. 22 is a first side schematic view of an accommodating intraocular lens assembly according to another exemplary embodiment of the present disclosure.
Figure 23:
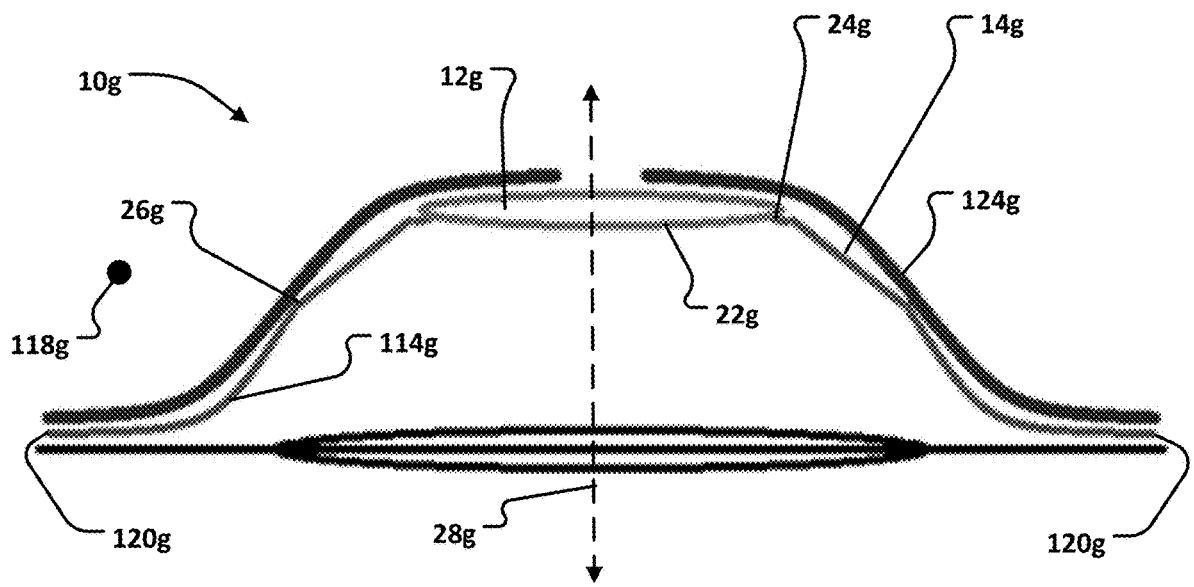
FIG. 23 is a second side view of the accommodating intraocular lens assembly shown in FIG. 22.

With reference now to FIGS. 22 and 23, an AIOL 10*g* includes a lens 12*g*, a stanchion 14*g*, and a shell 114*g*. The lens 12*g* can be centered on an optic axis 28*g* and can be configured for positioning in an eye. The lens 12*g* can have a first anterior side 20*g* and a first posterior side 22*g*. The first anterior side 20*g* can face toward a pupil 116*g* of the eye when the lens 12*g* is positioned in the eye. The first posterior side 22*g* can face away from the pupil 116*g* of the eye when the lens 12*g* is positioned in the eye.

The stanchion 14*g* can be frustoconical and have a distal end 24*g* connected to the lens 12*g* and can extend away from the lens 12*g* to a base end 26*f*. The stanchion 14*g* can appear substantially straight in a plane containing the optic axis 28*g*, the plane of view of FIGS. 22 and 23.

The shell 114*g* can have the shape of less than a full ring torus wherein the shell 114*g* extends three hundred and sixty degrees about the optic axis 28*g* in the toroidal direction and extends no greater than one hundred and eighty degrees about a poloidal center of curvature, referenced at 118*g* in FIG. 22. The shell 114*g* can have an outer perimeter 120*g* radially furthest from the optic axis 28*g* and an inner perimeter 122*g* radially closest to the optic axis 28*g*. The base end of the stanchion 14*g* can be connected to the inner perimeter 122*g*.

The lens 12*g*, the at least one stanchion 14*g*, and the shell 114*g* can be configured to be positioned in contact with an Iris 124*g* of the eye whereby contraction of the ciliary muscle during accommodation of the eye moves the Iris 124*g* against the shell 114*g* and causes the shell 114*g* to invert such that the poloidal center of curvature moves from a first side of the shell 114*g* along the optic axis 28*g* (shown in FIG. 22) to a second side of the shell 114*g* that is opposite to the first side of the shell 114*g* (shown in FIG. 23). Further, this causes the lens 12*g* to move in a direction collinear to the optic axis 28*g*. The dimensions of the shell 114*g* can be selected in view of several references that disclose the mathematical relationships necessary for "snapping" as shown in FIGS. 22 and 23. These references include "Curvature-Induced Instabilities of Shells" by Pezzulla et al.

U.S. Pat. Nos. 10,265,163 and 10,709,551 are hereby incorporated by reference for teachings related to the interaction between the ciliary muscle and stanchions to induce movement between lenses.

An AIOL according to an embodiment of the present disclosure can also include arcuate linking members extending such as disclosed in the '613 and '551 patents. The linking members are not required for all embodiments of the present disclosure but can be desirable for modulating the graph of CBA against IOLA. Duane's graph of accommodation with age is a well-established reference. The amplitude of accommodation is the increase in optical power that an eye can achieve in adjusting its focus. The "amplitude" is defined by a range of object distances for which the retinal image can be sharply. The larger the range of object distances, the larger the amplitude. The amplitude of accommodation is measured during an eye-examination. The closest that a normal eye can focus is typically about 10 cm for a child or young adult. Accommodation then decreases gradually with age, effectively finishing just after age fifty.

Duane's Curve shows that a pre-presbyopic individual (around age 40 or less) has a range or amplitude of accommodation of about 6 diopters or more. A diopter (us) is the unit of measurement of the optical power of a lens and is equal to the reciprocal of the focal length measured in meters (1/meters). It is thus a unit of reciprocal length. For example, a 2 diopter lens brings parallel rays of light to focus at ½ meter-1.

Therefore, an AIOL that merely produces the required degree of accommodation (IOLA) at maximal CBA for near work, has limited utility unless it also provides a smooth transition of accommodative power similar to that achieved by the pre-presbyopic crystalline lens. In fact having a high accommodative power may be a disadvantage if that power is invoked at low levels of CBA or is only available at the extreme accommodative effort because such variations of power may result in disorientating visual fluctuations. The stanchion designs set forth herein (width, flare, curvature, shape, variations in mechanical properties of composite material, etc.) assist in modulating the IOLA to CBA curve. This curve can also be adjusted post-operatively if necessary by application of energy such as laser.

The linking members can also assist with biocompatibility by preventing snagging and also help to minimize deviations from the desired final positions of the stanchions by linking and spacing them apart. The arcuate linking members can interconnect adjacent pairs of base ends. The arcuate linking members do not prevent adjacent base ends from moving relative to each other. The arcuate linking members can be a desirable feature during implantation of the assembly 10, to generally maintain the positions of the base ends. By permitting relative movement of the base ends, the arcuate linking members substantially do not hinder each stanchion from at least some relative movement.

In one or more embodiments of the present disclosure, one or more of the stanchions can contain fluid. The stanchion can be filled with fluid prior to implantation in the eye or after being implanted. When the stanchion is compressed, fluid is directable to another portion of the stanchion or to one of the lenses.

One or more embodiments of the present disclosure can be configured to support and hold (1) a biometric intraocular sensor to measure and transmit/display data such as intraocular pressure, (2) a drug delivery system to release medication within eye, (3) a mechanical supporting device particularly useful for the treatment of glaucoma by opening drainage channels for aqueous humor within the eye and/or for supporting and stabilizing ocular structures such as the iris or lens capsule to facilitate intraocular surgery, and/or (4) supporting an IOL especially an AIOL located either in the sulcus or the capsular bag being dual or single optic and modular or one-piece.

Embodiments of the present disclosure, including a ring member, stanchions, and the haptic passenger, should be made from biocompatible materials that fulfil necessary requirement so strength, flexibility and elastic memory, such requirements varying depending on the ring member morphology. Morphology options can include ring members empty in the center. The ring members may be empty centrally for purposes of modular attachment of haptic passengers so that their circumferences can be made oblate to allow insertion through an incision considerably smaller than their largest diameter in the relaxed state. Uniformly flexible ring members empty in the center can be squeezed into an oval shape or twisted into a figure-of-eight shape. Ring members can have varying flexibility, empty in the center with or without hinges arranged around their periphery. These ring members fold at specified junctions to deform into a heart shape or a double loop. Morphology options can also include ring members that are a solid disc shape. In such case they may be folded into a spiral cylindrical roll, a roughly semicircular (taco) shape along its diameter, concertina fashion through an injector, or a combination of these options to allow insertion through an incision considerably smaller than their largest diameter in the relaxed state.

An array of flexible stanchions can connect the two partly deformable ring members so that the structure can exist in three states. In a vivo state or relaxed state, pairs of stanchions are attached by their distal ends near the periphery of opposite ring members with each stanchion radiating away from the center of the ring and making contact with the base end of its paired stanchion. The paired stanchions are arranged so that they meet in a third plane between the planes of the two ring members. The junctions of the base ends of the stanchion pairs describe an approximate circle (maximum haptic circle) whose diameter is greater than either of the two ring members. The length, angle and flexibility of the stanchions is configured so that the maximum haptic circle matches the perimeter of the ocular anatomy to which the haptic carrier is to attach: anterior chamber angle, ciliary sulcus or capsular bag.

In a coiled state or packed state, the planes of the ring members are closely positioned to each other along the visual axis. In this state, the flexible stanchions are coiled and sequestered between the two ring members whose edges can be shaped so that they approximate a protected circular enclosure when the ring members are drawn closer by rotation. The purpose of the enclosure is to protect the coiled stanchions so that they will not cause damage to or be damaged by ocular structures during insertion and placement. The coiled state is achieved by the ring members being rotated relative to one another in an axis passing through their centers. The rotation has the effect of drawing in and straightening out the base stanchion junctions so that the diameter of the Maximum haptic circle is decreased. The ring member having a smaller diameter can serve as a bobbin around which the stanchions are wound.

The elastic and mechanical properties of the stanchion materials can be of a certain nature so that they coil and uncoil without slipping out of alignment, and a cylindrical frame may need to be placed within the stanchions to guide their coiling in the same manner that drums are used to wind cable. For optimal function a third ring may be used intermediate in size between the ring member having a larger diameter and the ring member having a smaller diameter, placed adjacent to the ring member having a smaller diameter. The third ring can serve as a frame with apertures through which the stanchions pass. Its function is to facilitate coiling or winding of the stanchions by laying and guiding them into proper position in an enclosed space between the third ring and the ring member having a smaller diameter.

In the coiled state, spontaneous uncoiling is prevented by one or both of two mechanisms can be prevented by the planes of the two ring members being in close alignment so that the uncoiling forces are contained by the rigidity of the ring member having a larger diameter until equilibrium is disrupted by the mechanical separation between the planes of the ring members, such as with the use of using a lever instrument of the type commonly used in ocular surgery. Uncoiling can also be prevented by a mechanical stopper such as a pin, knob or wedge that prevents relative movement between the ring members until it is removed.

In the third state, a transition state or insertion state, the coiled ring members can be grasped with an insertion instrument or placed within an injector cartridge so that their dimensions are suitable for passage through a small incision and placement within the eye. This state occurs after the coiled state and before the in vivo state. In this state, the ring members are either flattened if hollow in their center, or folded if not hollow in their center, such temporary deformation being necessary to maximize the ring diameters that may fit within the smallest desirable incision. If a mechanical stopper has been used to maintain the coiled state it is removed once the ring members have been deformed because spontaneous uncoiling is prevented by the deformation and the stopper is no longer necessary. Once the haptic carrier is placed in the desired location it is released and the deformed ring members return slowly to their "coiled state" shape. Once the haptic carrier is close to its coiled state, it will begin to spontaneously uncoil because of the absence of any mechanical stopper or because a lever instrument is then used to separate the ring members. As the planes of the ring members separate, the spontaneous uncoiling of the ring members will cause the stanchions to expand outwards in a plane between the ring member members until the proper anatomical location is reached.

Coiled ring embodiments could feasibly be packaged in the transition state after manufacture and such a "pre-loaded cartridge" has desirable features but has the drawback of placing high demands on the elastic memory of the material requiring relatively precise return to its original shape after having been stored in a stressed state for several months. A compromise solution could be to place and store the IOL inside a sealed cartridge in the unfolded state. The cartridge can be designed so that one side is attached to a syringe or plunger mechanism while the other side has a tapering fluted tube through which the IOL is pushed by the plunger once the tip of the tube has been placed into the incision. The design of the tube folds the IOL so that it fits through the narrow opening and then unfolds once in place.

Coiled-ring embodiments can provide several benefits. The stanchions can be protected by a sleeve during insertion and placement thus preventing crimping and breakage. Ocular structures can be protected by a sleeve so that a smooth profile is presented at sites of friction such as incision, iris and capsule thus preventing damage to these structures. A reduced arc of space is occupied during unfolding, which protects ocular structures. Because the haptic passenger only occupies one plane (in the empty center versions), abrasion against intra-ocular structures is minimized as the IOL unfolds. In prior art, unfolding of the IOL typically occurs in a sweeping arcuate fashion like the movements of wings, which requires a considerable amount of unobstructed volume within the eye if the IOL is not to touch ocular structures other than those it is designed to rest against. It is particularly important to minimize touch or abrasion against the inner lining of the cornea (endothelial layer) and the iris. The coiled ring design with empty center minimizes risk of endothelial cell damage due to uncoiling in one plane rather than arcuate sweep unfolding of prior art. In the case of a solid disc design, even though the IOL will occupy more than one plane when it is folded into a semicircle or taco, the fact that the stanchions will not expand outwards until the IOL has resumed an approximately flat discoid shape means that the volume of excursion within the eye will still be considerable less than in the prior art. Another benefit is that the coiled-ring arrangement can allow for multiple stanchion support (8 or more) rather than conventional two spring haptics or four point plate haptic resulting in better centration and greater stability and reduced risk of dislocation. Further, the coiled-ring arrangement minimizes the volume of material required for the IOL by use of a compact design that allows expansion after insertion, which is ideal for dual optic IOL (accommodating or even non-accommodating) and for modular IOL.

It is noted that one or more embodiments of the present disclosure can be formed from materials that can be modified after the lens assembly is implanted in the eye. For example, at least one mechanical property of at least one of the plurality of stanchions can be modified after the implanting. A mechanical property can at least partially define how the stanchion behaves under loading. In one or more embodiment, the modification can be carried out by applying electromagnetic energy to a portion of the at least one of the plurality of stanchions and thereby modifying an elasticity of the at least one of the plurality of stanchions.

One or more embodiments of the present disclosure can provide a Haptic design that maintains stability of its Haptic Passenger in the ciliary sulcus during ocular movement due to its shape and size. The haptic can be composed of stanchions which attach to the circumference of a fixed ring member at one end, and whose other ends describe a circular oval that forms a variable "virtual ring." The planar separation of the fixed ring member and the virtual ring can be dependent on the angles formed by the stanchions relative to the rings, while their lengths can remain essentially constant.

One or more embodiments of the present disclosure can prevent dislocation by gravity, inertia and flow of intraocular fluids, and mechanical forces exerted by adjacent intraocular structures both static and dynamic. The stability can be achieved by the size, shape, and/or composition of the haptic arrangement with the size being selected on the basis of pre-operative measurements made on each patient. The components that define the virtual ring (delineated by base end of stanchions) can be arranged so that they form a an oval circle of a variable diameter whose maximum extent corresponds to that of the ciliary sulcus (SSD) when CBA is relaxed and whose minimum extent corresponds to the diameter of the ciliary sulcus (SSD) when CBA is maximally activated. The said diameter can be oval shaped rather than strictly circular, to conform to the shape of the human ciliary sulcus.

The virtual ring of contact elements (base end of stanchions) can be made of a size and shape that fit securely into the ends of the ciliary sulcus without slippage or biological damage. The material can be bio-compatible and deformable but have sufficient structural memory to be folded prior to insertion into the eye through a small corneal incision and then unfolded into position within the ciliary sulcus of the eye.

The haptic design can thus be suited by dimensions and material of composition for stable and accurate surgical placement in the ciliary sulcus of the human eye between the anterior face of the lens capsule and zonules, and the posterior surface of the iris. A first anatomical change caused by CBA can be utilized by one or more embodiments of the present disclosure as shape-changing mechanisms is the decrease in diameter of the ciliary sulcus (perpendicular to the visual axis) due to annular contraction. This is measured as a decrease in the sulcus to sulcus diameter (SSD) which causes the virtual ring to contract, increasing separation of between fixed and virtual rings and so moving the fixed ring member and haptic passenger forward towards the cornea relative to the plane of the SSD circle. A second anatomical change can be anterior movement of the ciliary sulcus due to CB contraction. This causes forward movement of the plane of the SSD circle relative to the fixed points of the ocular globe caused by ciliary muscle contraction, resulting in forward movement of the virtual ring towards the cornea, which is additive in effect to the forward movement of the fixed ring member caused by reduction in SSD. A third anatomical change can be anterio-posterior pressure or compression at the ciliary sulcus between the zonules and the posterior surface of the iris due to forward movement of the ciliary body. Anterio-posterior pinching occurring in the ciliary sulcus due to annular contraction of the ciliary muscle results in increased compression at the ciliary sulcus from anatomical "crowding" against the posterior surface of the iris.

Ciliary sulcus placement effectively harnesses the three main functional elements of the ciliary muscle (longitudinal, oblique and annular) which on ciliary muscle contraction generate mechanical force that is matched to movements of single or multiple optic IOLS. Ciliary body contraction forces can be thus used to convert contraction to anterior displacement of the ring member of fixed circumference offset from the plane of the contracting circle. May be single or double (dual optic), convert contraction to move pins or pistons relative to a tangential bar or ring, and squeeze fluid. This allows a single or dual optic design in the configuration whereby equatorial reduction in circumference of an approximately circular anatomical trench associated with the ciliary muscle allows purchase on multiple contact points causing a corresponding reduction in circumference of the circle joining the contact points so that the contact pints contract in relation to each other without the need for sliding relative to the circular anatomical trench. The contact points serving as hinges whose relative movement is translated into variation of optical power to allow for close focusing on objects when accommodation is voluntarily initiated by contraction of the ciliary muscle. The movement described can be either increased separation of multiple optics of the IOL or forward movement of the center of a single optic.

One or more embodiments of the present disclosure can provide a Haptic design that is well suited for safe insertion through a small incision by being composed of multiple spoke like flexible elements arranged in a radial fashion connecting at least one fixed ring member to a virtual ring.

One or more embodiments of the present disclosure can define a star-like structure with individual radii converging at a central *nexus* to support a Haptic Passenger. Intermediate radii can be joined by a circular band of varying width and thickness running tangentially to the radii serving to shield and space out the elements, provide redundant support for safety, and prevent protrusions or deformations that catch against biological structures during injection and unfolding, presenting a planar profile for insertion into ciliary sulcus. The periphery of the radii can serve as contact points against anchoring structures within the eye.

The anterior-posterior hinged struts (stanchions) incorporated into "cogwheel" shaped sheets joined at edges are amenable to work in the ciliary sulcus. The requirement of predictable flexibility and elastic memory retention in response to small variations in mechanical forces needed when the lens is in situ, conflicts with the requirement for extreme deformability needed to fold and unfold the lens. The designs and shapes described above is best suited to overcome these difficulties.

Other benefits include efficient mechanical linkage with ciliary body contraction whether placed in capsular bag or ciliary sulcus. Multiple, flexible interconnected struts provide error correction for asymmetry and minor mis-positioning as well as some redundancy in case of damage during insertion. Small bulk allows for easy folding for insertion. Further, the performance does not depend on integrity of capsular bag (or zonules when placed in sulcus).

One or more embodiments of the present disclosure can provide a Haptic design that moves in harmony with internal ocular structures. The haptic flexes, contracts, expands and changes shape in a reversible manner in response to, and while in apposition with dynamic intraocular structures such as annular muscles, elastic capsules, supporting fibers and ocular connective tissue without presenting mechanical resistance that may damage ocular structures during such repeated and reversible mechanical changes.

A desirable aspect of one or more embodiments of the present disclosure can be point-to-point contraction linking (PPCL) in which the contact points are multiple enough to distribute force and support, spaced horizontally, vertically and all other important intermediate meridians, and large enough to provide support and make contact without damage but small enough and/or curved to offer minimal resistance to and friction against elastic dynamically contracting intra-ocular structures such as annular muscles or elastic capsules.

One or more embodiments of the present disclosure can provide a Haptic design whose cyclic movements in response to internal ocular structures can be used to predictably alter the force, tension and spatial separation between its constituent elements.

One or more embodiments of the present disclosure can provide a Haptic design composed of elements that are rigid and connected at certain points but flexible and elastically jointed at others so that may move in relation to one another and the eye but maintain stable fixation overall once implanted in the eye.

One or more embodiments of the present disclosure can provide a Haptic design that compresses in response to CB contraction in a predictable manner without significantly impeding CB contraction by virtue of point-to-point deformability. By thus compressing in response to CB contraction, one or more embodiments of the present disclosure can provide a Haptic design that links anatomical changes occurring during CBA, to variations in mechanical forces between the elements of the haptic. By virtue of the variation of force, tension and spacing between the elements of the rigid but elastically jointed haptics applies forces on the Haptic Passenger.

One or more embodiments of the present disclosure can provide a Haptic design in which the cyclic variations of force, tension and separation between its constituent elements can be linked to predictable variations in the properties of the Haptic Passenger. In the specific case where the Haptic Passenger is an optical lens system or "optic," the power of the optic can be reversibly and predictably varied through various mechanisms depending on the design of the lens system.

An approach for predictably and reversibly varying optical power in an IOL that is focused for distance in the non-accommodative state in order to achieve IOLA (beyond pseudo-accommodation) in various biologically feasible IOL systems include a "Simple lens." The power of a simple lens can be reversibly varied by changing its location relative to the optical center of the eye by vaulting or moving forward during CBA. This is achieved in the Jester's collar design (ring member with stanchions having decreasing width away from the ring member) by forward movement of the optic caused by point-to-point contraction.

An approach for predictably and reversibly varying optical power in an IOL that is focused for distance in the non-accommodative state in order to achieve IOLA (beyond pseudo-accommodation) in various biologically feasible IOL systems also includes a "Compound lens." The power of a dual optic IOL can be reversibly varied by changing the separation of the optics. This can be achieved through the double Jester's collar design or in the single Jester's collar design by any other means whereby one optic is fixed closer to the haptics at their contact points and the other optic further away so that CB contraction results in separation of the two optics.

An approach for predictably and reversibly varying optical power in an IOL that is focused for distance in the non-accommodative state in order to achieve IOLA (beyond pseudo-accommodation) in various biologically feasible IOL systems also includes a "Flexible lens." The power of a flexible lens can be reversibly varied by pinching, squeezing or compressing the flexible periphery of the lens to cause increased power by increasing the relative curvatures or relative separation of the anterior and posterior surfaces. In the Jester's Collar design this effect can be achieved by giving the optic element a flexible periphery and mounting it between the flaps of the collar (the stanchions extending away from the ring member) so that points on the flexible periphery are attached to the inner surface of the haptic elements and become compressed during CBA, in turn compressing the periphery and achieving the desired power change.

An approach for predictably and reversibly varying optical power in an IOL that is focused for distance in the non-accommodative state in order to achieve IOLA (beyond pseudo-accommodation) in various biologically feasible IOL systems also includes a "Biological lens." A biological lens as described for the purposes of the present disclosure is that which most closely approximates the natural, youthful crystalline lens of the human eye. Technological constraints have hitherto prevented the manufacture of such a lens for prosthetic use. If such prosthesis could be manufactured and assembled within the eye, it could be fixed in place between the haptic elements in the same fashion as that described for the flexible lens above and could have its power reversible varied in the same fashion by compression of its periphery between the haptics.

An approach for predictably and reversibly varying optical power in an IOL that is focused for distance in the non-accommodative state in order to achieve IOLA (beyond pseudo-accommodation) in various biologically feasible IOL systems also includes a "Neo-biological lens." A neo-biological lens as described for the purposes of the present disclosure would be an IOL whose power can be varied by electronic or photo-chemical means either across the entire material of the lens, or selectively in certain regions. Practical application of this type of lens is limited by the available technology, but should it be manufactured, its power could be controlled in many ways by the haptic linked to CBA as described above.

One or more embodiments of the present disclosure can provide a Haptic design which when manufactured to the appropriate dimensions is well suited for placement within the capsular bag of the eye. One or more embodiments of the present disclosure can provide a Haptic design allowing for attachment of the Haptic Passenger after the Haptic has been implanted in the eye so that the Haptic can be placed within the eye before the insertion of the Haptic Passenger. One or more embodiments of the present disclosure can provide a Haptic design that when placed prior to capsule rhexis provides stability and support of the lens capsule, which facilitates the performance of surgery. One or more embodiments of the present disclosure can provide a Haptic design that when placed prior to capsule rhexis can be adapted to improve pupillary dilation and thus facilitates the performance of surgery.

For desirable placement and harnessing of the ciliary body power, it may be desirable to have a two component IOL system in which the haptic passenger (a single or dual optic IOL) is attached within the eye to a ring-shaped haptic. The haptic itself is circular flat disc open in the center which can be implanted in the ciliary sulcus after an incision is made but before the anterior capsule is opened (capsulorhexis, or simply rhexis). This ring would confer some additional benefits in performance of the surgery such as maintaining AC depth and preventing rapid fluctuations to protect zonules, holding anterior capsule taught to improve capsulorhexis, providing a potential platform for (detachable) iris hooks or iris lip to improve pupillary dilation, providing secure anchor linked to ciliary sulcus to against which optic/haptic complex can be placed to transmit kinetic force of ciliary muscle contraction and convert it to optical changes in IOL power, and providing a ring member for potential post-operative mechanical/optical property modification by selective application of laser energy.

One or more embodiments of the present disclosure can provide a haptic that can be implanted separately from the haptic passenger, which has the advantage that it can be placed within the eye without the optic (or other haptic passenger). If the haptic passenger does not present an obstruction to surgery (such as that presented by a centrally located optic), it may be implanted at an earlier stage of surgery and thus facilitate subsequent steps of the surgical procedure. The modular IOL allows a two stage implantation. A first benefit of the two stage implantation are that it allows the haptic to be securely placed and seated in the ciliary sulcus before further surgical steps distort the anatomy around the ciliary sulcus. A haptic unfolded behind the iris is almost certain to become located in the ciliary sulcus because its posterior migration is limited by the anterior surface of a lens. It cannot pass beyond the anterior capsule, as the anterior capsule of the lens is still intact at this stage of the surgery. A second benefit is that the haptic can incorporated benefits of other surgical devices without the separate need for these devices, such as pupil expanders and anterior chamber stabilizing rings.

Design considerations for haptic in modular (two stage) IOL system include the area of touch wherein the slant of ring member and curve of the stanchions can be optimized by mathematical modeling to enhance refractive change per unit of ciliary muscle contraction, optic configurations such as can use single, dual or multiple optic configurations to simulate accommodation, allowing the ring member to have a gap (open or horseshoe shape) to allow for easier introduction past iris and assist with iris displacement or be a continuous circle, the inside edge can have a groove to accommodate optic, and the optic can have lip to fix against ring member at one end and two other lips or snaps to fix into place.

One or more embodiments of the present disclosure can provide a Haptic design that occupies and stretches the area adjacent to the ciliary body of the eye in a manner that may increase aqueous humor outflow and treat glaucoma following surgery. This is a novel concept and does not rely on a modular, two stage IOL (or any of the other elements of the ring member design other than ciliary sulcus placement) but on the design of the stanchion elements and interconnecting bands/rings so that they cause stretching and tension at a specific point near the base of the iris to open the aqueous humor drainage channels of the eye. The goal is to mimic an effect of certain glaucoma medicines that achieve the same result by causing contraction of the ciliary muscle. Perfection of this embodiment will require description of the optimum design of the base end of the haptics that sit in the sulcus, and perhaps other embellishments so it may best to allude to it in case details distract from the AIOL functioning.

One or more embodiments of the present disclosure can provide a Haptic design that allows for post-operative adjustment of amplitude of IOLA by selective application of energy to its elements to alter their elasticity, tension, relative separation placement within the eye.

One or more embodiments of the present disclosure can provide a Haptic design that allows for post-operative adjustment of lens spherical and or toric power by selective application of energy to its elements to alter their elasticity, tension, relative separation placement within the eye. Embellishments made possible by selective application of energy to the haptics through dilated pupils include the ability to modify spherical power, the ability to modify toric power, and the ability to modify asphericity.

An optic design (either as a single optic design or one or both of a dual optic design) which can be incorporated into a single stage or modular IOL system and which can be part of an AIOL or conventional IOL in which the Haptic Passenger is an optic in the form of a flexible lens system having a periphery containing components that can expand or contract in response to selective application of energy, whose expansion and contraction alters the central curvature and thickness of the lens. Embellishments made possible by selective application of energy at the periphery of at least one of the optics through dilated pupils include the selective application of energy at the optic periphery can alter the optical properties of the lens optic by increasing the pinching action of rivet type supports connecting the anterior and posterior surfaces of an optic, separated by a viscolelastic fluid. This arrangement allowing post-operative treatment that allows modification of the following lens optical properties: spherical power, cylindrical (Toric) power and axis to correct astigmatism, and correction of irregular astigmatism and higher order optical aberrations.

There are a number of stanchion contact designs used to translate the mechanical forces generated by CBA into IOLA by enhancing optic movement contemplated by the present disclosure including various contact designs, rigidity changes and curvatures.

One or more embodiments of the present disclosure can provide a Haptic design that by virtue of allowing later attachment of the Haptic Passenger also allows for its own injection into the eye in the form of a helical strip. The flexible strip may be inserted into the eye using an instrument or injector and once injected into the eye forms a closed circular ring, forms a "C" shaped ring, or forms a 'C" shaped ring whose ends can be joined to form a closed circular ring.

One or more embodiments of the present disclosure can provide a Haptic design that by virtue of allowing later attachment of the Haptic Passenger also allows for its own insertion into the eye through a small incision in the form of a circle with at least four points of elastic articulation. This method of articulating the relatively rigid segments of the circle allows the Haptic to fit through a narrow incision whilst maintaining enough rigidity to be guided behind the iris and preventing excessive disruption of the space between the iris and the lens capsule.

Because of the anatomy of the ocular globe, a small corneal incision, if constructed in a step like fashion at the correct location with a special instrument, can be self-sealing so that the pressure of fluid within the eye will keep it closed until it heals. The upper limit to the length of such an incision is generally considered to be no more than about three millimeters. It can be desirable that an IOL optic be at least about five millimeters in diameter to focus light on the retina. A smaller optic could cause glare, reflections, and other troublesome symptoms. To span the diameter of the capsular bag or ciliary sulcus and desirably be suspend the optic in place, the distance between opposite ends of the haptics can be about nine millimeters (in the case of the sulcus) and about twelve millimeters (in the case of capsular bag placement). Any device that requires stable placement in the sulcus or capsular bag will likely be subject to these constraints. Therefore, any IOL, however complex or elegant in design, will have extremely limited utility unless it can be placed within the eye through a small incision and also meet the minimum size requirements of the optic and haptic diameters. Several other anatomical and physiological factors place practical constraints on intraocular device design. Embodiments of the present disclosure can meet these practical constraints and provide patentable utility.

In some embodiments, the intended haptic passenger can be a single optic IOL. The embodiment can be one piece. The embodiment can include a single ring member. The single ring member can be continuous. The mechanism of morphological change allowing for entry of the single ring member through small corneal incision can be limited by the incorporated IOL optic, which should be in the shape of a disc, plate or star that is folded. Fold configurations may be like a taco, roll, or concertina. Each fold method can use forceps or an injector cartridge. The enhanced mechanism for accurate stanchion placement once the embodiment is inside the eye can be a star-shaped profile of the haptic (a result of the ring member and stanchions), distinct rounded contact points defined by the base ends of the stanchions, with connections between the base ends presenting a rounded planar profile with intervening fenestrations to allow flexing of the haptic and the flow of intraocular fluids. The nature of the optics (the optical properties) can be adjustable after surgery.

In some embodiments, the intended haptic passenger can be a single optic IOL. The embodiment can be one piece. The embodiment can include more than one ring member. Each of the ring members can be continuous. The mechanism of morphological change allowing for entry of the single ring member through small corneal incision can be limited by the incorporated IOL optic, which should be in the shape of a disc, plate or star that is folded. Fold configurations may be like a taco, roll, or concertina. Each fold method can use forceps or an injector cartridge. The enhanced mechanism for accurate stanchion placement once the embodiment is inside the eye can be an uncoiling motion, such as could occur with the embodiment shown in FIG. 13. The nature of the optics can be adjustable after surgery. Optic rotation during CBA would defeat some of the modification utility (especially astigmatism adjustment) unless the embodiment when uncoiled was configured to allow movement of the optics without rotation.

In some embodiments, the intended haptic passenger can be a single optic IOL that is modular. The ring member and stanchions can be one component and the haptic passenger can be mounted on the ring member and stanchions after the ring member and stanchions have been positioned in the eye. The embodiment can include a single ring member that is continuous. The mechanism of morphological change allowing for entry of the single ring member and stanchions through small corneal incision can be uniform flexibility, where the ring member and stanchions are deformable and placed behind iris with forceps or injector and released to unfold into position. Alternatively, the mechanism of morphological change can be rigid arcs separated by hinges, defining a collapsible ring member. The nature of the optics can be adjustable after surgery.

In some embodiments, the intended haptic passenger can be a single optic IOL that is modular. The ring member and stanchions can be one component and the haptic passenger can be mounted on the ring member and stanchions after the ring member and stanchions have been positioned in the eye. The embodiment can include a single ring member and the single ring member can each be discontinuous. The mechanism of morphological change allowing for entry of the single ring member through small corneal incision can be the ring member being a horse shoe shape. The ring member can be at least partially elastic and flexible. One end of the ring member can be placed into the anterior chamber through the incision, guided behind dilated iris, and the trailing end can then be guided through incision in a horizontal "Fosbury flop" manner so that ring member only has to flex partially. Alternatively, the embodiment can be implanted with an injector cartridge. The at least partially-flexible ring member can be placed into a curved syringe-type injector. A plunger can be used to push the embodiment into the eye, which reforms its curve as its leading end is guided under the iris. The curve and rotation of the injector assists in laying down the embodiment into place. The injector tip can be rotated to allow placement with minimal trauma. The nature of the optics can be adjustable after surgery.

In some embodiments, the intended haptic passenger can be a single optic IOL that is modular. The ring member and stanchions can be one component and the haptic passenger can be mounted on the ring member and stanchions after the ring member and stanchions have been positioned in the eye. The embodiment can include more than one ring member and the ring members can each be continuous. The mechanism of morphological change allowing for entry of the ring members through a small corneal incision can be can be uniform flexibility, where the ring member and stanchions are deformable and placed behind iris with forceps or injector and released to unfold into position. The enhanced mechanism for accurate stanchion placement once the embodiment is inside the eye can be a star-shaped profile of the haptic (a result of the ring member and stanchions), distinct rounded contact points defined by the base ends of the stanchions, with connections between the base ends presenting a rounded planar profile with intervening fenestrations to allow flexing of the haptic and the flow of intraocular fluids. The enhanced mechanism for accurate stanchion placement once the embodiment is inside the eye can be an uncoiling motion, such as could occur with the embodiment shown in FIG. 13. Alternatively, the mechanism of morphological change can be rigid arcs separated by hinges, defining a collapsible ring member. The nature of the optics (the optical properties) can be adjustable after surgery. The nature of the optics can be adjustable after surgery.

In some embodiments, the intended haptic passenger can be a multi-optic IOL that is one-piece or modular. Such embodiments can include a single ring member or more than one ring members. The rings of a one-piece or modular embodiment can be continuous. For one-piece embodiments, the mechanism of morphological change allowing for entry of the single ring member through small corneal incision can be limited by the incorporated IOL optic, which should be in the shape of a disc, plate or star that is folded. Fold configurations may be like a taco, roll, or concertina. Each fold method can use forceps or an injector cartridge. The enhanced mechanism for accurate stanchion placement once the embodiment is inside the eye can be a star-shaped profile of the haptic (a result of the ring member and stanchions), distinct rounded contact points defined by the base ends of the stanchions, with connections between the base ends presenting a rounded planar profile with intervening fenestrations to allow flexing of the haptic and the flow of intraocular fluids. The enhanced mechanism for accurate stanchion placement once the embodiment is inside eye can also be an uncoiling motion, such as could occur with the embodiment shown in FIG. 13. The nature of the optics can be adjustable after surgery. Optic rotation during CBA would defeat some of the modification utility (especially astigmatism adjustment) unless the embodiment when uncoiled was configured to allow movement of the optics without rotation. The nature of the optics can be can be adjustable after surgery.

In some embodiments of the present disclosure, a plurality of stanchions can be interconnected with a ring member and the embodiment can omit a lens. Such an embodiment can be implanted in a patient's eye without a lens. Such an embodiment can be placed in the ciliary sulcus and thereby increase aqueous humor outflow by stretching open the trabecular meshwork. Such an embodiment, when placed in the ciliary sulcus, can also decrease aqueous humor production by ciliary body. Any of the structural embodiments of the present disclosure can be placed in the ciliary sulcus without a lens.

The term "coiling" has been used herein for the process of retracting stanchions relative to lenses, prior to insertion in the eye. The terms "folding" and "rolling" has been used for processes applied to an AIOL after the stanchions have been coiled. An AIOL can be elastically deformed by folding or by rolling in order to place the AIOL in a tool for subsequent insertion in the capsular bag or in the ciliary sulcus. As shown in the Figures of the present disclosure, the tool can be introduced through a small incision. One benefit enjoyed by various embodiments of the present disclosure is the completion of unfolding when the AIOL is in situ, which can serve as the mechanical trigger that unlocks the uncoiling of the stanchions since only discs that are roughly flat and parallel can spin relative to each other for the purposes of uncoiling. The temperature change and/or hydration experienced by the AIOL, once it is in the eye, can also be utilized to make the unfolding and uncoiling more controlled and atraumatic to the intraocular structures, by selecting material with appropriate biochemical properties.

Figure 24:
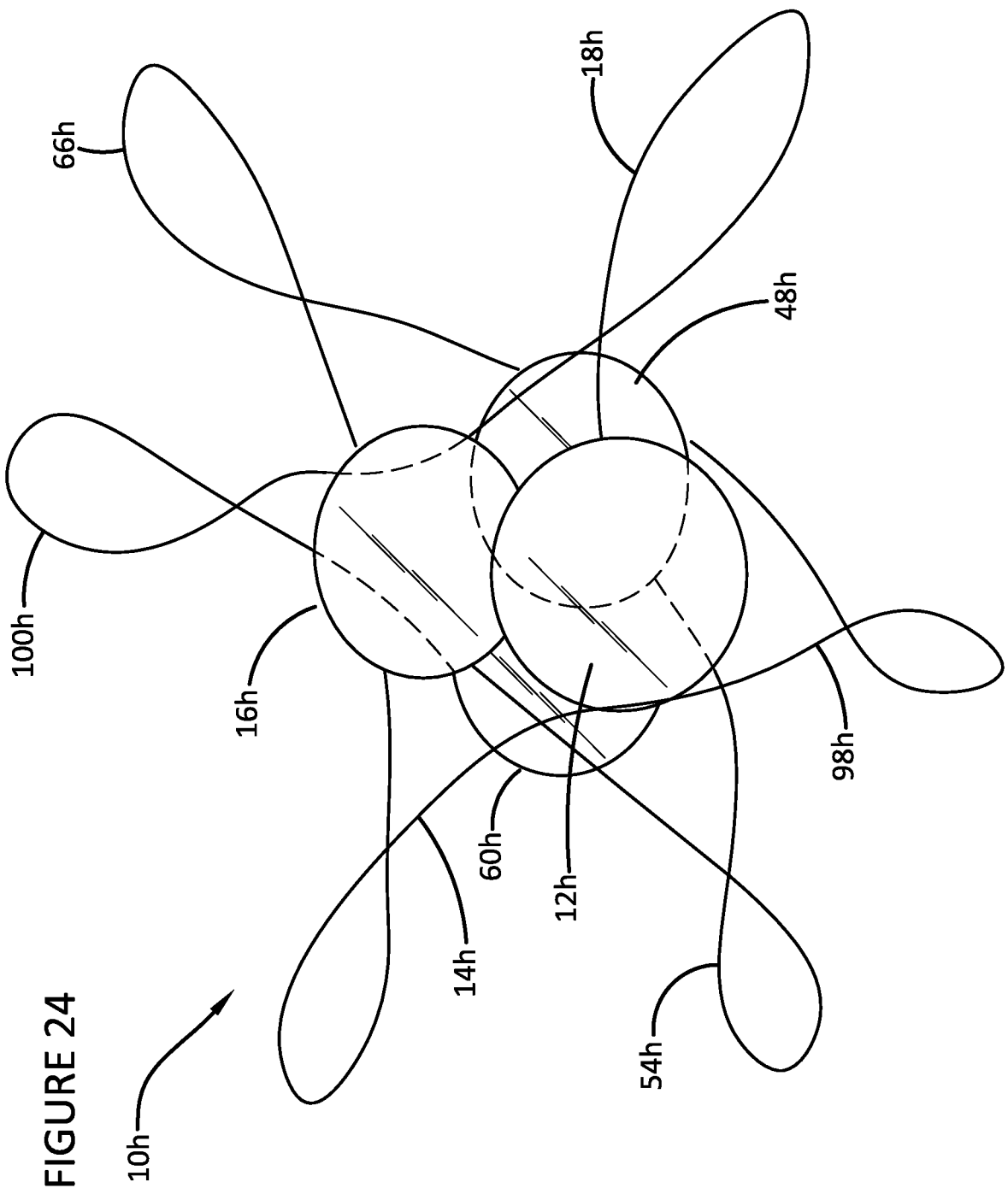
FIG. 24 is a schematic front view of an accommodating intraocular lens assembly according to another exemplary embodiment of the present disclosure.
Figure 25:
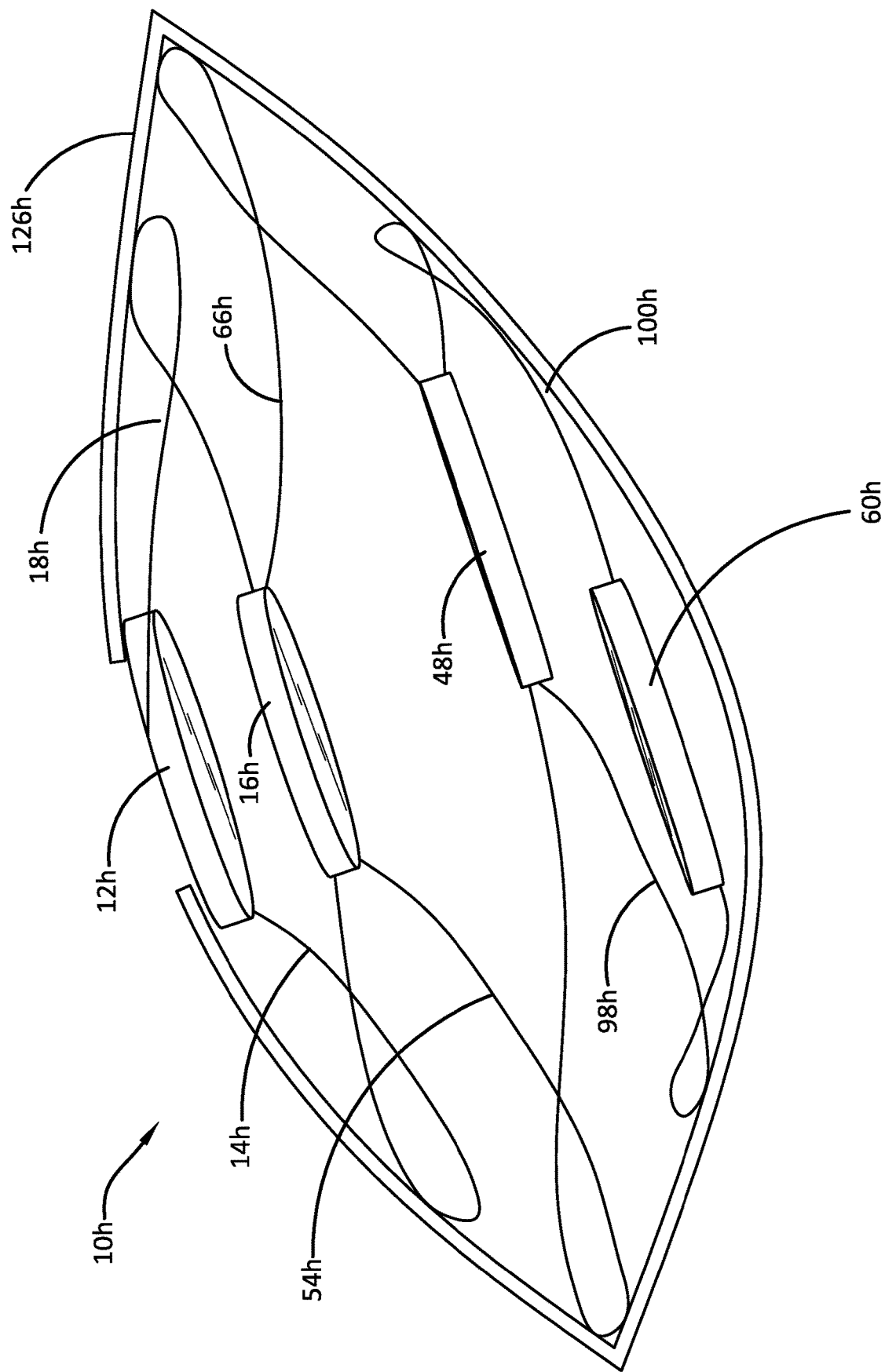
FIG. 25 is an isometric view of the embodiment shown in FIG. 24 positioned in a capsular bag during disaccommodation.
Figure 26:
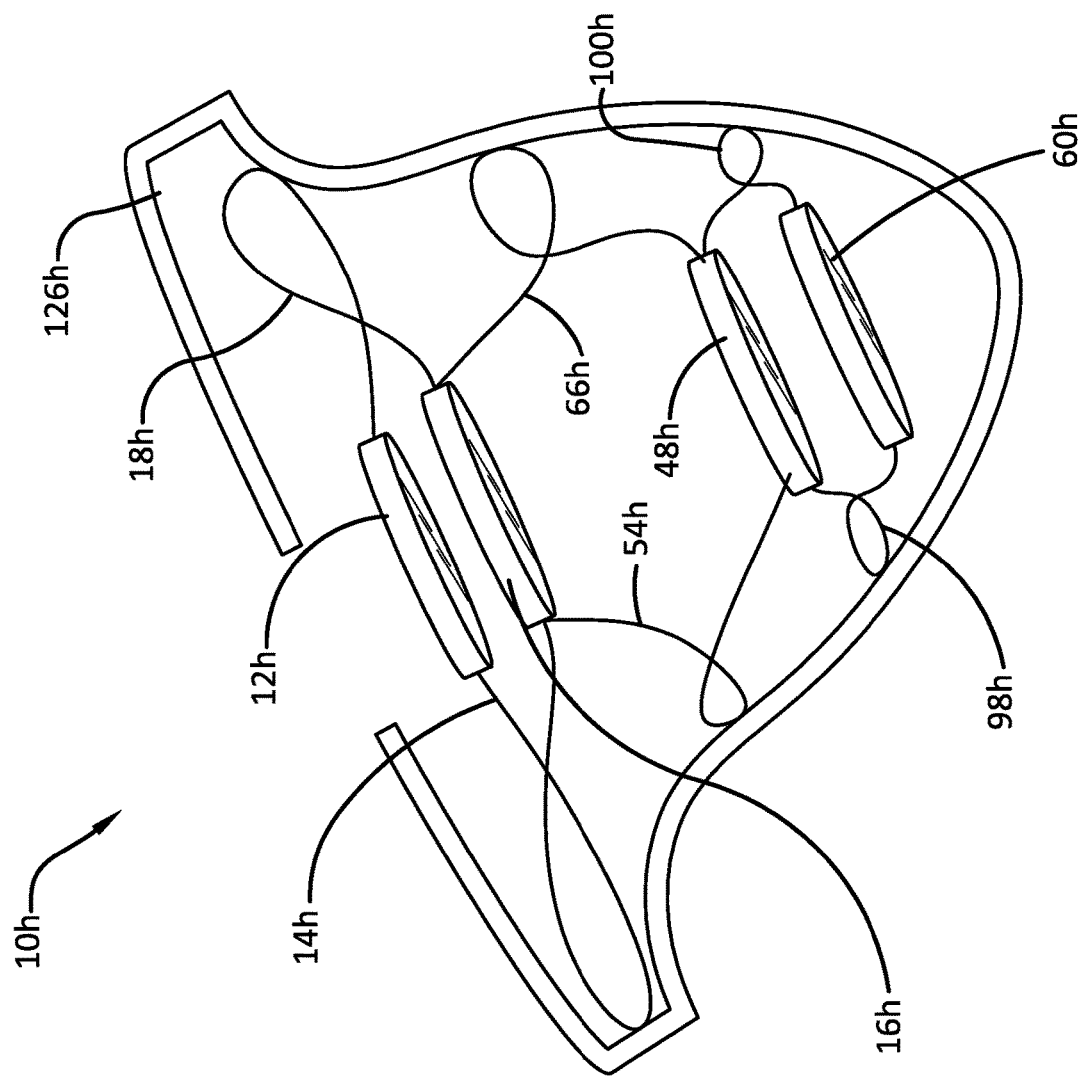
FIG. 26 is a side view of the embodiment shown in FIGS. 24 and 25 positioned in the capsular bag during accommodation.

With reference now to FIGS. 24-26, in another exemplary embodiment of the present disclosure, an AIOL 10*h* includes a first lens 12*h*, a first stanchion 14*h*, a second stanchion 18*h*, a second lens 16*h*, a third stanchion 54*h*, a fourth stanchion 66*h*, a third lens 48*h*, a fifth stanchion 98*h*, a sixth stanchion 100*h*, and a fourth lens 60*h*. The first and second stanchions 14*h*, 18*h* extend between the first and second lenses 12*h*, 16*h*. The third and fourth stanchions 54*h*, 66*h* extend between the second and third lenses 16*h*, 48*h*. The fifth and sixth stanchions 98*h*, 100*h* extend between the third and fourth lenses 48*h*, 60*h*.

FIG. 25 is an isometric view of the AIOL 10*h* positioned in a capsular bag 126 during disaccommodation (when the ciliary muscle is relaxed). FIG. 26 is a side view of the AIOL 10*h* positioned in the capsular bag 126 during accommodation. FIGS. 25 and 26 demonstrate that the respective stanchions 14*h*, 18*h*, 54*h*, 66*h*, 98*h*, 100*h* can be configured (material, shape, rigidity, orientation, etc.) to laterally move the lenses 12*h*, 16*h*, 48*h*, 60*h* with respect to one another and also move the lenses 12*h*, 16*h*, 48*h*, 60*h* along the optic axis of the eye as well. Further, the respective stanchions 14*h*, 18*h*, 54*h*, 66*h*, 98*h*, 100*h* can be configured such that lenses 12*h*, 16*h*, 48*h*, 60*h* group in pairs and the pairs separate from one another, taking advantage of decreased tension in the capsular bag 126 when the ciliary muscle contracts.

While the present disclosure has been described with reference to an exemplary embodiment, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the appended claims. The right to claim elements and/or subcombinations that are disclosed herein is hereby unconditionally reserved. The use of the word "can" in this document is not an assertion that the subject preceding the word is unimportant or unnecessary or "not critical" relative to anything else in this document. The word "can" is used herein in a positive and affirming sense and no other motive should be presumed. More than one "invention" may be disclosed in the present disclosure; an "invention" is defined by the content of a patent claim and not by the content of a detailed description of an embodiment of an invention.

What is claimed is:

1. An accommodating intraocular lens assembly comprising:
   a first lens configured for positioning in an eye and having a first anterior side and a first posterior side, said first anterior side facing toward a pupil of the eye when said first lens is positioned in the eye and said first posterior side facing away from the pupil of the eye when said first lens is positioned in the eye;
   a first stanchion having a first distal end connected to said first lens and extending away from said first lens to a first base end, said first base end configured for positioning within a capsular bag of the eye or in a ciliary sulcus or on a ciliary muscle of the eye whereby contraction of the ciliary muscle during accommodation of the eye moves said first base end towards an optic axis of the eye;
   a second lens configured for positioning in the eye with said first lens and having a second anterior side and a second posterior side, said second anterior side facing said first posterior side when said first lens and said second lens are positioned in the eye and said second posterior side facing into to the eye when said second lens is positioned in the eye;
   a second stanchion having a second distal end connected to said second lens and extending away from said second lens to a second base end, said second base end configured for positioning within the capsular bag of the eye or in the ciliary sulcus or on the ciliary muscle of the eye whereby contraction of the ciliary muscle during accommodation of the eye moves said second base end towards the optic axis of the eye; and
   wherein said first lens and said second lens move laterally relative to one another during contraction of the ciliary muscle in a vertically-extending plane containing the optic axis of the eye and substantially centered in the eye, the lateral relative movement further defined as lateral relative to the optic axis.

2. The accommodating intraocular lens assembly of claim 1 wherein said first posterior side of said first lens and said second anterior side of said second lens are in contact with one another and slide across one another during contraction of the ciliary muscle, the sliding across one another occurring during the lateral relative movement that is lateral relative to the optic axis.

3. The accommodating intraocular lens assembly of claim 1 wherein said first anterior side of said first lens and said second posterior side of said second lens are mirrored in shape with respect to one another in the vertically-extending plane.

4. The accommodating intraocular lens assembly of claim 1 wherein at least one of said first anterior side of said first lens and said second posterior side of said second lens defines a wavy surface in the vertically-extending plane, said wavy surface including at least one crest and at least one trough.

5. The accommodating intraocular lens assembly of claim 4 wherein both of said first anterior side of said first lens and said second posterior side of said second lens define respective wavy surfaces in the vertically-extending plane.

6. The accommodating intraocular lens assembly of claim 5 wherein said first lens, said first stanchion, said second lens, and said second stanchion are configured such that:
   when the ciliary muscle is relaxed said at least one crest of said wavy surface of said first anterior side of said first lens is substantially aligned in the vertically-extending plane with said at least one trough of said wavy surface of said second posterior side of said second lens; and
   when the ciliary muscle is contracted said at least one crest of said wavy surface of said first anterior side of said first lens is substantially aligned in the vertically-extending plane with said at least one crest of said wavy surface of said second posterior side of said second lens.

7. The accommodating intraocular lens assembly of claim 1 further comprising:
   a third lens configured for positioning in the eye and having a third anterior side and a third posterior side, said third anterior side facing toward the pupil of the eye when said third lens is positioned in the eye and said third posterior side facing away from the pupil of the eye when said third lens is positioned in the eye;
   a third stanchion having a third distal end connected to said third lens and extending away from said third lens to a third base end, said third base end configured for positioning within the capsular bag of the eye or in the ciliary sulcus on the ciliary muscle of the eye whereby contraction of the ciliary muscle during accommodation of the eye moves said third base end towards an optic axis of the eye;
   a fourth lens configured for positioning in the eye with said third lens and having a fourth anterior side and a fourth posterior side, said fourth anterior side facing said third posterior side when said third lens and said fourth lens are positioned in the eye and said fourth posterior side facing into to the eye when said fourth lens is positioned in the eye;
   a fourth stanchion having a fourth distal end connected to said fourth lens and extending away from said fourth lens to a fourth base end, said fourth base end configured for positioning within the capsular bag of the eye or in the ciliary sulcus or on the ciliary muscle of the eye whereby contraction of the ciliary muscle during accommodation of the eye moves said fourth base end towards the optic axis of the eye;
   wherein said third lens and said fourth lens move laterally relative to one another during contraction of the ciliary muscle in a horizontally-extending plane containing the optic axis of the eye and perpendicular to the vertically-extending plane;
   wherein said third anterior side of said third lens faces said second posterior side of said second lens; and
   wherein, when said first lens and said second lens and said third lens and said fourth lens are positioned in the eye, said first stanchion and said second stanchion are spaced substantially one hundred and eighty degrees from one another about the optic axis, said third stanchion and said fourth stanchion are spaced substantially one hundred and eighty degrees from one another about the optic axis, and said first stanchion and said third stanchion are spaced substantially ninety degrees from one another about the optic axis.

8. The accommodating intraocular lens assembly of claim 7 wherein:
said first anterior side defines a first wavy surface in the vertically-extending plane including at least one first crest and at least one first trough;
said second posterior side of said second lens defines a second wavy surface in the vertically-extending plane including at least one second crest and at least one second trough;
said first lens, said first stanchion, said second lens, and said second stanchion are configured such that when the ciliary muscle is relaxed said at least one first crest of said first wavy surface of said first anterior side of said first lens is substantially aligned in the vertically-extending plane with said at least one second trough of said second wavy surface of said second posterior side of said second lens and when the ciliary muscle is contracted said at least one first crest of said first wavy surface of said first anterior side of said first lens is substantially aligned in the vertically-extending plane with said at least one second crest of said second wavy surface of said second posterior side of said second lens;
said third anterior side defines a third wavy surface in the horizontally-extending plane, said third wavy surface including at least one third crest and at least one third trough;
said fourth posterior side of said fourth lens defines a fourth wavy surface in the horizontally-extending plane including at least one fourth crest and at least one fourth trough; and
said third lens, said third stanchion, said fourth lens, and said fourth stanchion are configured such that when the ciliary muscle is relaxed said at least one third crest of said third wavy surface of said third anterior side of said third lens is substantially aligned in the horizontally-extending plane with said at least one fourth trough of said fourth wavy surface of said fourth posterior side of said fourth lens and when the ciliary muscle is contracted said at least one third crest of said third wavy surface of said third anterior side of said third lens is substantially aligned in the horizontally-extending plane with said at least one fourth crest of said fourth wavy surface of said fourth posterior side of said fourth lens.

9. The accommodating intraocular lens assembly of claim 8 wherein, when the ciliary muscle is contracted, said at least one first crest of said first wavy surface of said first anterior side of said first lens, said at least one second crest of said second wavy surface of said second posterior side of said second lens, said at least one third crest of said third wavy surface of said third anterior side of said third lens, and said at least one fourth crest of said fourth wavy surface of said fourth posterior side of said fourth lens are substantially centered on the optic axis of the eye.

10. The accommodating intraocular lens assembly of claim 1 further comprising:
a third lens configured for positioning in the eye and having a third anterior side and a third posterior side, said third anterior side facing said second posterior side of said second lens and said third posterior side facing away from the pupil of the eye when said third lens is positioned in the eye;
a third stanchion having a third distal end connected to said third lens and extending away from said third lens to a third base end, said third base end configured for positioning within the capsular bag of the eye or in the ciliary sulcus or on the ciliary muscle of the eye whereby contraction of the ciliary muscle during accommodation of the eye moves said third base end towards an optic axis of the eye; and
wherein said first stanchion and said second stanchion and said third stanchion are evenly spaced from one another about the optic axis.

11. The accommodating intraocular lens assembly of claim 1 wherein at least one of said first lens and said second lens includes an optical metasurface.

* * * * *